(12) United States Patent
Levy et al.

(10) Patent No.: US 10,307,254 B2
(45) Date of Patent: Jun. 4, 2019

(54) BONE STRUCTURAL DEVICE

(75) Inventors: Mark M Levy, Raanana (IL); Shimon Spector, Matan (IL); Eyal Teichman, Hod Hasharon (IL); Elad Sapir, Kfar Yona (IL); Gal Amar, Rakefet (IL)

(73) Assignee: CoreLink, LLC, St. Louis, MO (US)

( * ) Notice: Subject to any disclaimer, the term of this patent is extended or adjusted under 35 U.S.C. 154(b) by 1084 days.

(21) Appl. No.: 14/130,950

(22) PCT Filed: Jul. 5, 2012

(86) PCT No.: PCT/US2012/045495
§ 371 (c)(1),
(2), (4) Date: Jul. 22, 2014

(87) PCT Pub. No.: WO2013/006669
PCT Pub. Date: Jan. 10, 2013

(65) Prior Publication Data
US 2014/0358246 A1 Dec. 4, 2014

Related U.S. Application Data

(60) Provisional application No. 61/504,330, filed on Jul. 5, 2011, provisional application No. 61/504,331, filed on Jul. 5, 2011.

(51) Int. Cl.
*A61F 2/28* (2006.01)
*A61F 2/44* (2006.01)
(Continued)

(52) U.S. Cl.
CPC ................ *A61F 2/28* (2013.01); *A61F 2/442* (2013.01); *A61F 2/4455* (2013.01); *A61F 2/4603* (2013.01); *A61F 2/4611* (2013.01); *A61F 2/30734* (2013.01); *A61F 2002/2835* (2013.01); *A61F 2002/3055* (2013.01); *A61F 2002/30062* (2013.01); *A61F 2002/30365* (2013.01);
(Continued)

(58) Field of Classification Search
CPC ....................................... A61F 2/44–2002/4495
See application file for complete search history.

(56) References Cited

U.S. PATENT DOCUMENTS

| | | | | |
|---|---|---|---|---|
| 5,390,683 A | * | 2/1995 | Pisharodi | A61F 2/442 128/898 |
| 6,126,689 A | * | 10/2000 | Brett | A61F 2/4455 623/17.15 |

(Continued)

FOREIGN PATENT DOCUMENTS

| | | |
|---|---|---|
| DE | 10344019 | 5/2005 |
| EP | 1552797 | 7/2005 |

(Continued)

OTHER PUBLICATIONS

PCT Written Opinion PCT/US2012/045495, dated Feb. 22, 2013.

*Primary Examiner* — Zade Coley
(74) *Attorney, Agent, or Firm* — Stinson Leonard Street LLP

(57) ABSTRACT

A bone structural device including a plurality of bone structural segments (40), wherein adjacent bone structural segments (40) are pivotally connected to one another about a pivot axis, and the bone structural segments (40) are expandable in height, which is in a direction generally parallel to the pivot axis.

5 Claims, 25 Drawing Sheets

(51) Int. Cl.
*A61F 2/46* (2006.01)
*A61F 2/30* (2006.01)

(52) U.S. Cl.
CPC ............ *A61F 2002/30372* (2013.01); *A61F 2002/30405* (2013.01); *A61F 2002/30433* (2013.01); *A61F 2002/30441* (2013.01); *A61F 2002/30448* (2013.01); *A61F 2002/30451* (2013.01); *A61F 2002/30461* (2013.01); *A61F 2002/30462* (2013.01); *A61F 2002/30471* (2013.01); *A61F 2002/30472* (2013.01); *A61F 2002/30476* (2013.01); *A61F 2002/30484* (2013.01); *A61F 2002/30505* (2013.01); *A61F 2002/30515* (2013.01); *A61F 2002/30538* (2013.01); *A61F 2002/30556* (2013.01); *A61F 2002/30568* (2013.01); *A61F 2002/30573* (2013.01); *A61F 2002/30578* (2013.01); *A61F 2002/30579* (2013.01); *A61F 2002/30601* (2013.01); *A61F 2002/30624* (2013.01); *A61F 2002/30649* (2013.01); *A61F 2002/30841* (2013.01); *A61F 2002/4415* (2013.01); *A61F 2002/4627* (2013.01); *A61F 2002/4693* (2013.01); *A61F 2002/4694* (2013.01); *A61F 2210/0014* (2013.01); *A61F 2250/0007* (2013.01); *A61F 2310/00011* (2013.01); *A61F 2310/00023* (2013.01); *A61F 2310/00952* (2013.01); *A61F 2310/00976* (2013.01)

(56) References Cited

U.S. PATENT DOCUMENTS

| | | | | |
|---|---|---|---|---|
| 6,174,334 B1 * | 1/2001 | Suddaby | ............... | A61F 2/4455 623/17.11 |
| 6,193,757 B1 * | 2/2001 | Foley | .................... | A61F 2/4455 623/17.16 |
| 6,833,006 B2 * | 12/2004 | Foley | .................... | A61F 2/4455 623/17.11 |
| 7,784,141 B2 * | 8/2010 | Knopow | ................. | A47L 13/38 15/209.1 |
| 7,905,920 B2 * | 3/2011 | Galea | .................... | A61F 2/4455 623/17.11 |
| 8,486,148 B2 * | 7/2013 | Butler | .................... | A61F 2/447 623/17.16 |
| 2002/0026244 A1 | 2/2002 | Trieu | | |
| 2003/0040746 A1 * | 2/2003 | Mitchell | ............ | A61B 17/1606 623/17.11 |
| 2006/0041258 A1 * | 2/2006 | Galea | .................... | A61F 2/4455 16/221 |
| 2006/0142858 A1 * | 6/2006 | Colleran | ............... | A61F 2/4465 623/17.11 |
| 2006/0224241 A1 * | 10/2006 | Butler | ................ | A61B 17/8858 623/17.15 |
| 2008/0125865 A1 * | 5/2008 | Abdelgany | ............. | A61F 2/447 623/17.16 |
| 2008/0147193 A1 * | 6/2008 | Matthis | ................. | A61F 2/4425 623/17.16 |
| 2008/0221384 A1 * | 9/2008 | Chi Sing | ............... | A61N 5/1015 600/7 |
| 2008/0243255 A1 * | 10/2008 | Butler | ................... | A61F 2/4465 623/17.16 |
| 2009/0012623 A1 | 1/2009 | Sack | | |
| 2009/0024217 A1 * | 1/2009 | Levy | ................. | A61B 17/8858 623/17.16 |
| 2009/0048676 A1 * | 2/2009 | Fabian, Jr. | ............. | A61F 2/442 623/17.16 |
| 2009/0143859 A1 * | 6/2009 | McClellan, III | ....... | A61F 2/4455 623/17.16 |
| 2009/0182431 A1 * | 7/2009 | Butler | ..................... | A61F 2/447 623/17.16 |
| 2009/0240335 A1 | 9/2009 | Arcenio | | |
| 2009/0281628 A1 * | 11/2009 | Oglaza | ............... | A61B 17/7065 623/17.15 |
| 2011/0066192 A1 | 3/2011 | Frasier | | |
| 2011/0144753 A1 | 6/2011 | Marchek | | |
| 2012/0271422 A1 * | 10/2012 | Miller | .................... | A61F 2/447 623/17.16 |

FOREIGN PATENT DOCUMENTS

| | | | |
|---|---|---|---|
| WO | 2005/009299 | 2/2005 | |
| WO | 2007/009123 | 1/2007 | |
| WO | WO 2007009123 A2 * | 1/2007 | ......... A61B 17/7208 |
| WO | 2007/022194 | 2/2007 | |
| WO | 2007/084239 | 7/2007 | |
| WO | 2007/121320 | 10/2007 | |
| WO | 2008/103781 | 8/2008 | |
| WO | 2010/129846 | 11/2010 | |

* cited by examiner

FIG. 2A
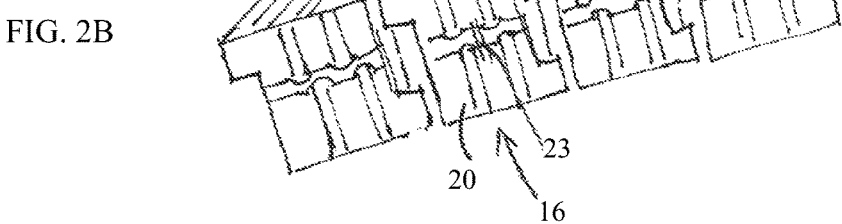
FIG. 2B
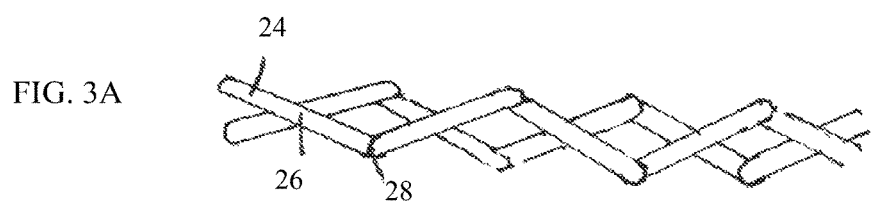
FIG. 3A
FIG. 3B
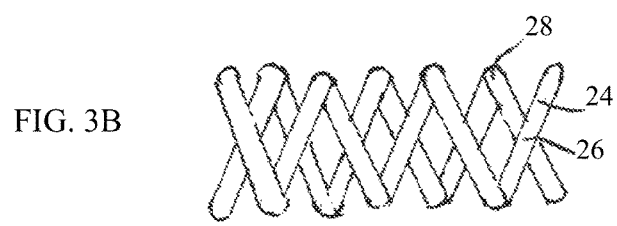
FIG. 4
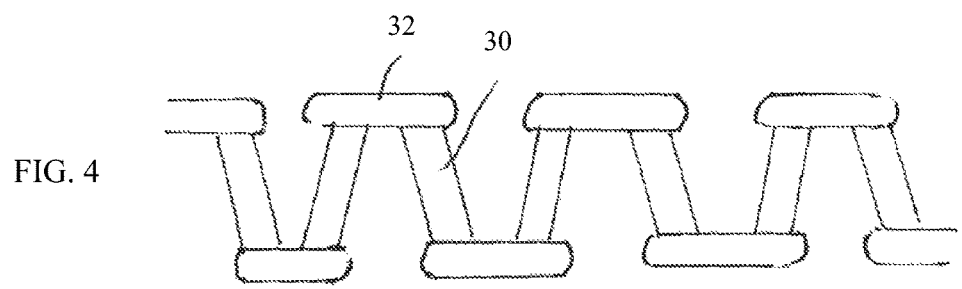

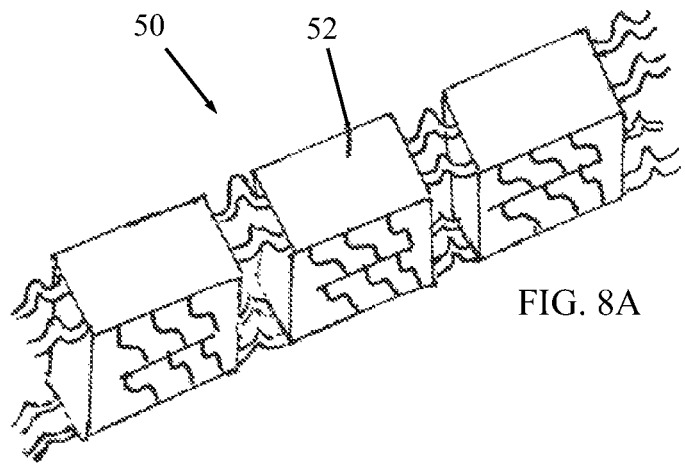
FIG. 8A
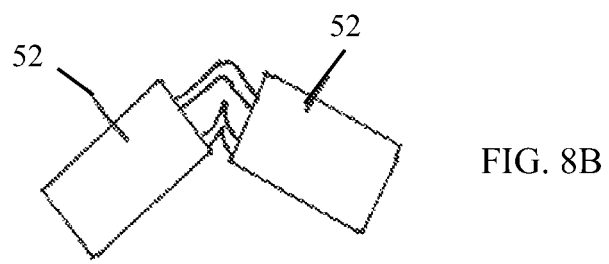
FIG. 8B
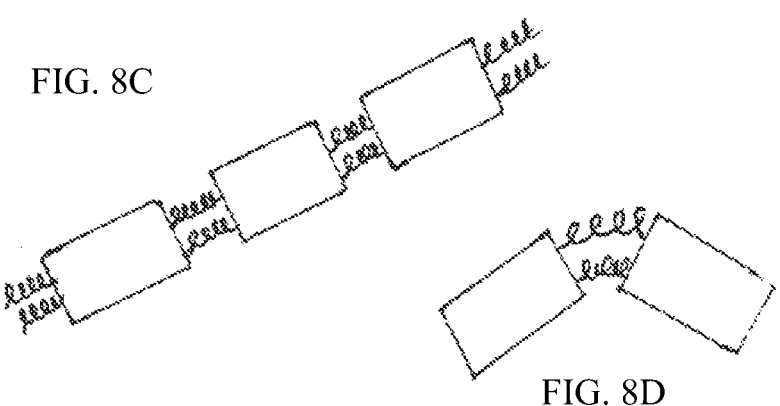
FIG. 8C
FIG. 8D

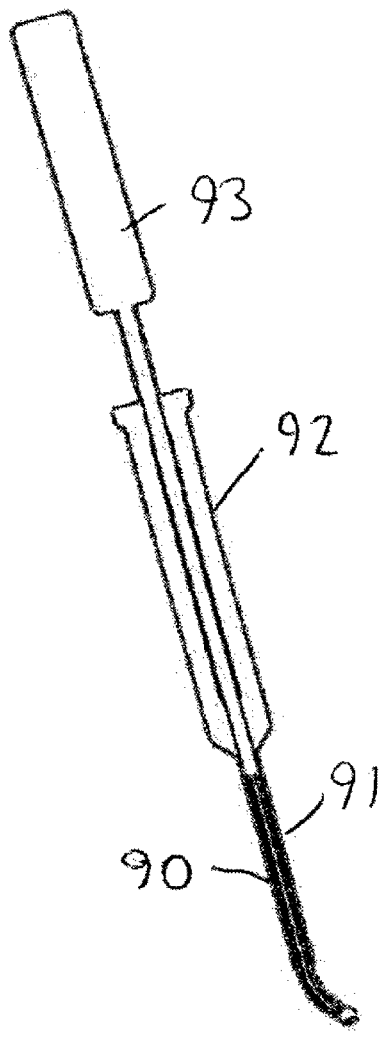
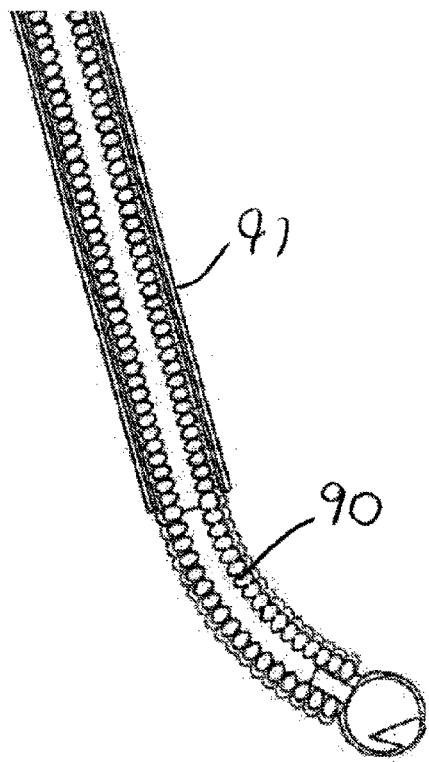
FIG. 9A                    FIG. 9B

FIG. 13C
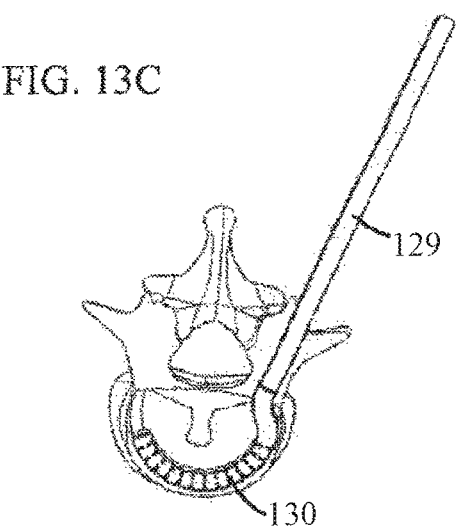
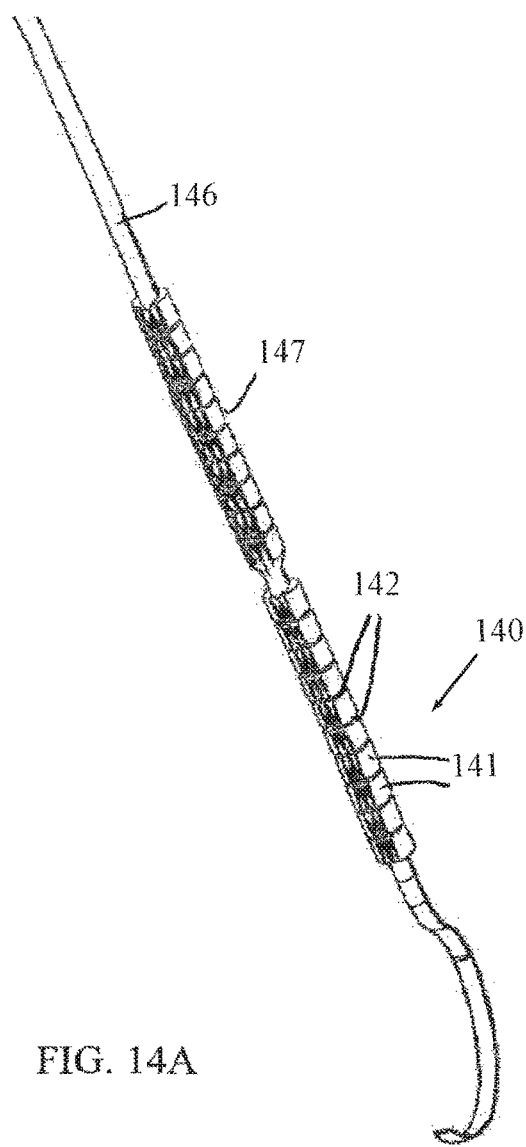
FIG. 14A

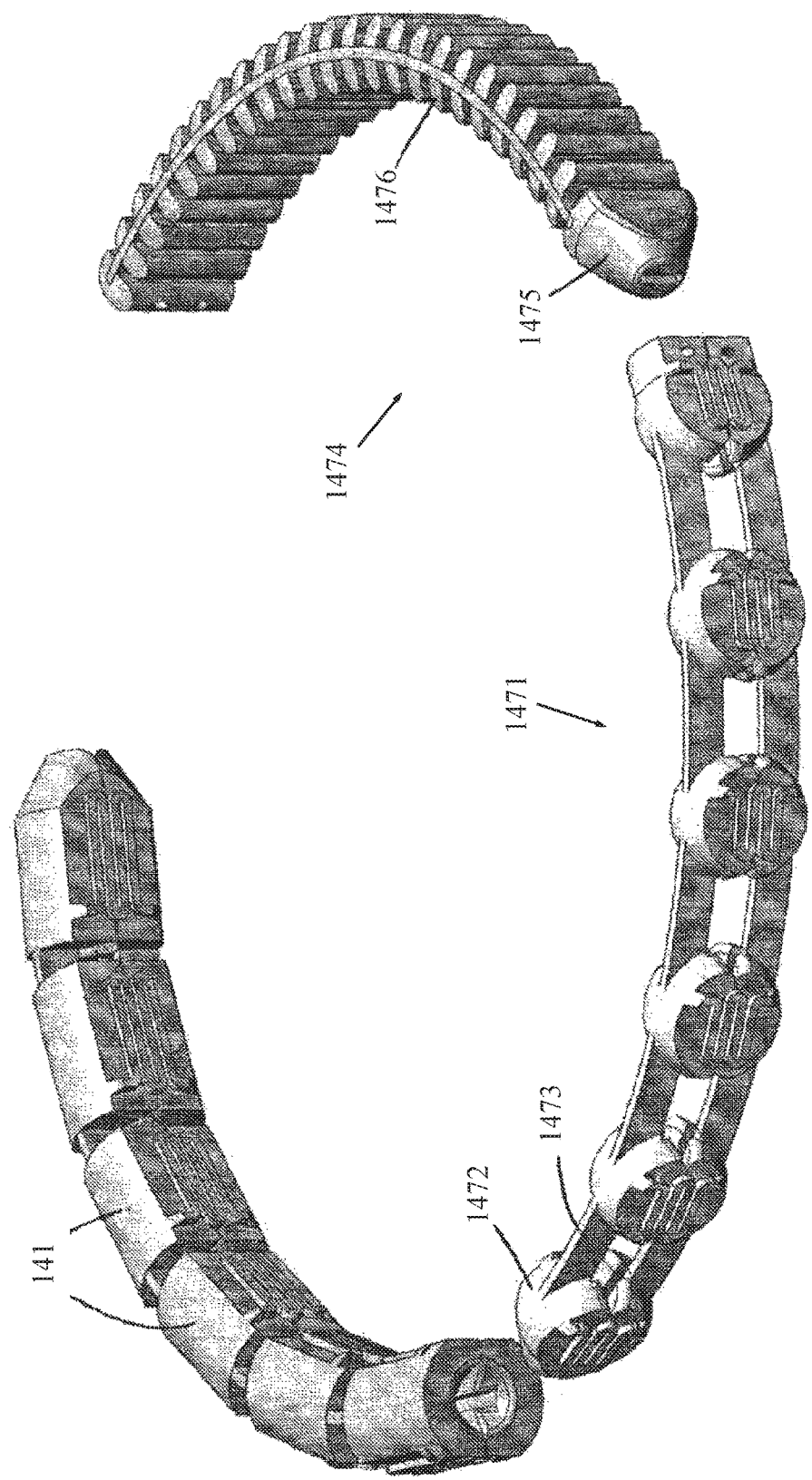

BONE STRUCTURAL DEVICE

FIELD OF THE INVENTION

The present invention relates generally to medical devices, and, more particularly, to implantable devices used to strengthen or support bony structures in the body, such as but not limited to, intervertebral or intravertebral devices to stabilize the human spine.

BACKGROUND OF THE INVENTION

The spinal column is a highly flexible structure comprising bones and connective tissue. Although the spine is capable of multiple degrees of motion, spinal injuries or anatomical irregularities may result in spinal pathologies that limit this range of motion.

Implant devices, such as vertebral spacers, intravertebral or intervertebral fusion devices and disc replacement devices, have been developed to assist with stabilization and fixation or functional support of the spine. Examples include pre-assembled rings, cages, boxes, dowels, and wedges of varying size and construction, such as meshes or plates, movable disc surfaces, gel or polymer spacers, elastomers and structures. However, all existing devices have certain drawbacks, such as difficulty of construction, insertion, bulkiness, inadequate surface coverage in area and/or height, multiple sizes (inventory) and others.

PCT/US2007/077495 describes an interbody spacer implant assembly for interbody fusion in a vertebral body and a method of insertion comprises a plurality of links and an elongated connector mechanism adapted to retain the plurality of links and allow the plurality of links to articulate with respect to one another.

SUMMARY OF THE INVENTION

The present invention seeks to provide novel implantable devices used to strengthen or support bony structures in the body, such as but not limited to, intravertebral or intervertebral fusion devices, as is described more in detail further below.

The devices of the invention can serve as a platform for use in the spine as an expandable cage for spine fusion and for intra-vertebral use for VCF (vertebral compression fracture) repair. Another embodiment is a device for use as a disc replacement device, a dynamic application allowing movement. The devices of the invention include MIS (minimal invasive surgery)/cannulated (or not cannulated) devices delivered over a guide wire, with expandable capability for height control (to regain disc space height or vertebral body height). The devices of the invention provide ample coverage of disc space, joint space, inner vertebral body or other bone, with a good foot print and a small portal of entry.

In one embodiment of the invention, units connected like a train are installed with a delivery system that can be manipulated for positioning and sequential deployment of one or more units or deployment of the train as a whole. The train-style units can be a closed structure, e.g., a sleeve or a tube that is closed to itself. The closed structure of the deployed train-style units can produce a virtual central space than can be filled (perhaps, in a dynamic application, mimicking the annulus fibrosis of a natural intervertebral disc; in the case of a spine fusion or vertebral fractures, the filler will allow bone formation; otherwise bone cement or substitutes can be also used). The device can be installed through just one side of the vertebra in a minimal invasive way (but delivery at both sides is also possible). Materials include, without limitation, hard or soft, non-resorbable, resorbable, natural or synthetic, biological, mixed, including metal, polymers, bone (allograft or other), PEEK (polyetheretherketone), cells, tissue culture products, PET (polyethylene terephthalate), nylon, DACRON, KEVLAR, PE (polyethylene), PTFE (polytetrafluoroethylene), polyester, memory alloys or polymers, PMMA, etc., or combinations thereof.

In another embodiment the structure can be installed though one side and left open but located near the cortical wall of the broken bone, to rebuild the lost original vertebra structure, as in the anterior and lateral walls of the vertebral body in a compression fracture with an anterior wedge shape. Any of those embodiments may include additional ways or attachments to further connect the device to the bone (other than surface contact), allowing a stand-alone static or a dynamic function, depending on the desired application.

The devices of the invention have other uses in bones in other parts of the skeleton besides the spine. For example, the device can be used as a bone spacer/filler in different bone locations, and can also be introduced in between bones or joint spaces when fusion or arthrodesis is attempted or for bone reconstruction proposes. As another example, in a dynamic application, the device can be used as a MIS (minimally invasive surgery) temporary or definitive total joint replacement device, partial joint replacement device, joint spacer or meniscus replacement device. The devices can be used with bone graft, biological bone cement, bone substitutes, gels, polymers, PMMA or combinations, etc. to enhance attachment to bone surface.

BRIEF DESCRIPTION OF THE DRAWINGS

The present invention will be understood and appreciated more fully from the following detailed description, taken in conjunction with the drawings in which:

FIGS. 2A and 2B are simplified illustrations of a bone structural device, in accordance with an embodiment of the present invention, including segments made of first and second members linked to each other by hinges, in respective contracted and expanded positions.

FIGS. 3A and 3B are simplified illustrations of a bone structural device, in accordance with an embodiment of the present invention, including hinged cross members, in respective contracted and expanded positions.

FIG. 4 is a simplified illustration of a bone structural device, in accordance with an embodiment of the present invention, including segments linked on alternating sides by flat links.

FIGS. 8A-8D are simplified illustrations of a bone structural device, in accordance with an embodiment of the present invention, including segments pivotally linked to one another by elastic (spring-like) members and plastically deformed links.

FIGS. 9A and 9B are simplified, partially cutaway illustrations of an insertion device with a flexible, jointed bone support device of the present invention.

FIG. 13C is a simplified perspective illustration of either of the bone support devices of FIG. 13A or 13B inserted into a vertebral structure or disc space, in accordance with an embodiment of the present invention.

FIGS. 14A and 14B are simplified perspective illustrations of a flexible bone (dynamic) support device, constructed and operative in accordance with an embodiment of the present invention, respectively before and after expansion.

FIGS. 14E-14F are simplified illustrations of an embodiment having multiple pusher elements for expanding bone structural segments.

DETAILED DESCRIPTION OF EXEMPLARY EMBODIMENTS

The devices of the invention may be used in minimal invasive surgery and/or open surgery of the spine, and are suitable also for other bone or joint locations.

In the spine location, for spine fusion, the device may be used as a cage in the disc space. The device may be used for vertebral body fractures, such as intravertebral VCF repair. In other embodiments, the device may be used in intervertebral disc treatment as a disc replacement device alone or in conjunction with a nucleus pulposus replacement.

The insertion of the device may be done from only one side of the vertebra (disc space or pedicle), via a posterior or posterolateral (or transforaminal) approach, as a minimally invasive technique, but also a lateral or anterior approach if desired, or in an open procedure. It can be used also from two sides of the vertebra or disc space if it is necessary to introduce two devices or to assemble two sections inside from two directions.

Previous to the insertion of the device, the space in the bone, the disc space or other location may be prepared by cleaning the material in the desired spot. In addition, distraction of the space to regain desired height can be previously achieved by a suitable instrument before the actual insertion of the device. In some embodiments the invention will provide the desired height without the need of previous manipulation.

Figure 1A:
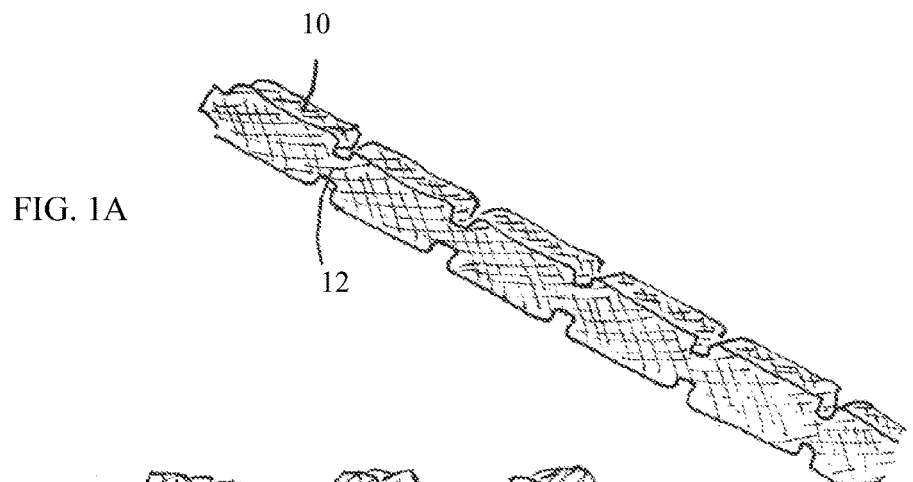
FIG. 1A is a simplified illustration of a bone structural device, constructed and operative in accordance with an embodiment of the present invention, including a series of segments interconnected by resilient links.
Figure 1B:
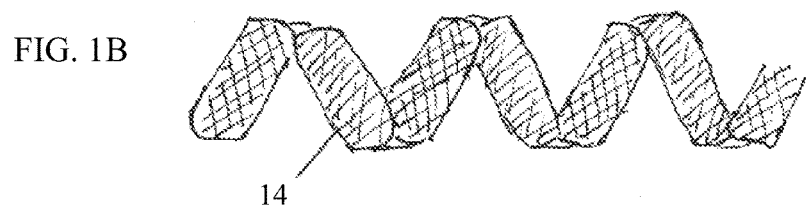
FIGS. 1B and 1C are simplified illustrations of bone structural devices, in accordance with two embodiments of the present invention, including segments formed as a spiral or helical spring.
Figure 1C:
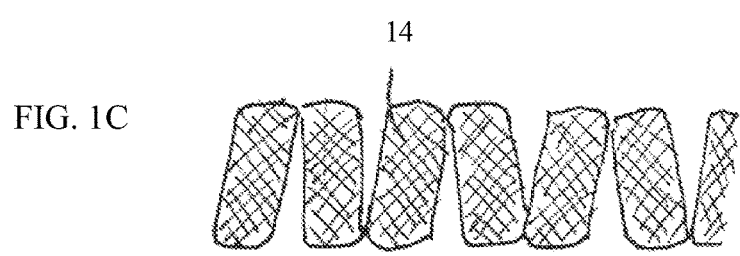
Figure 1D:
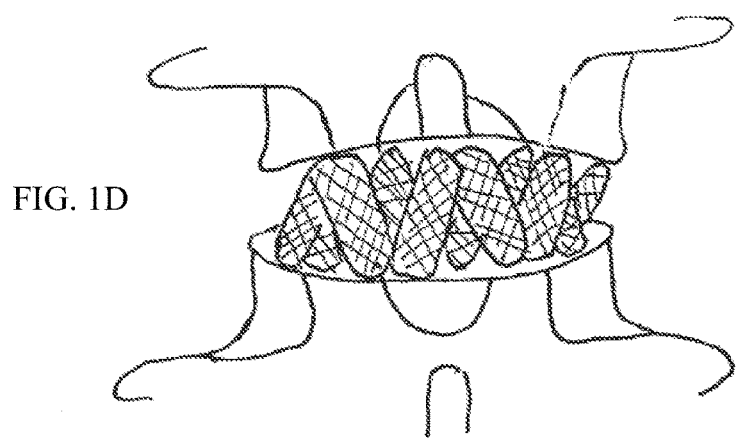
FIG. 1D is a simplified illustration of the bone structural device of FIGS. 1B and 1C installed in an intervertebral space.
Figure 5A:
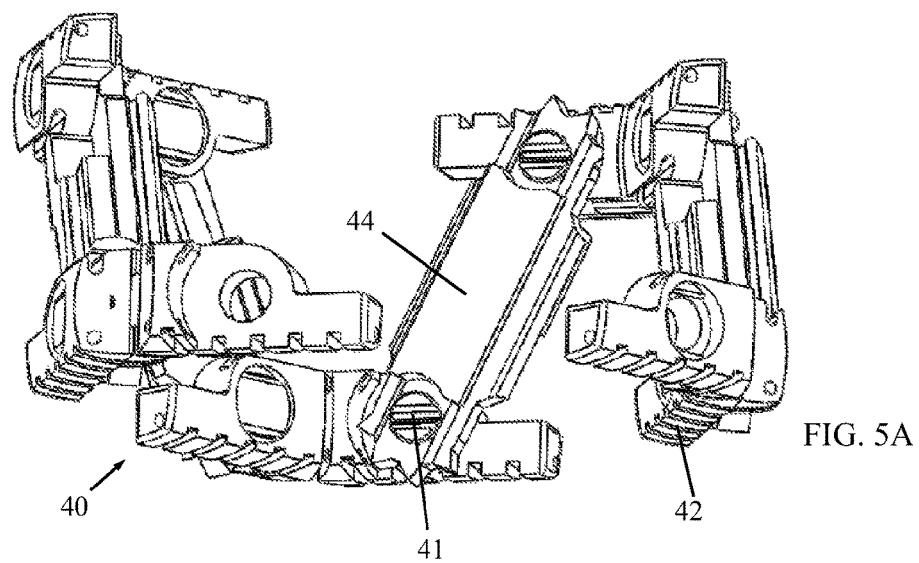
FIGS. 5A-5E are simplified illustrations of a bone structural device, in accordance with an embodiment of the present invention, including segments pivotally linked to one another by mechanical fasteners.
Figure 5B:
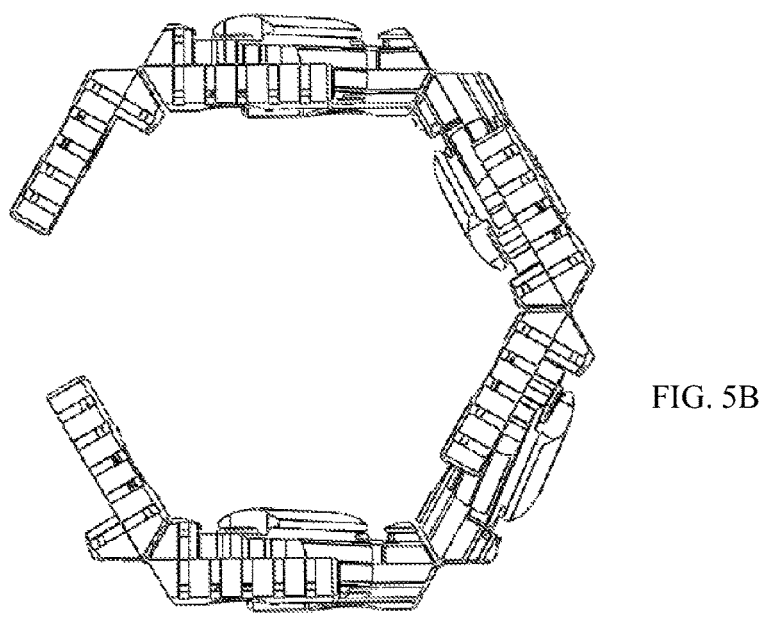
Figure 5C:
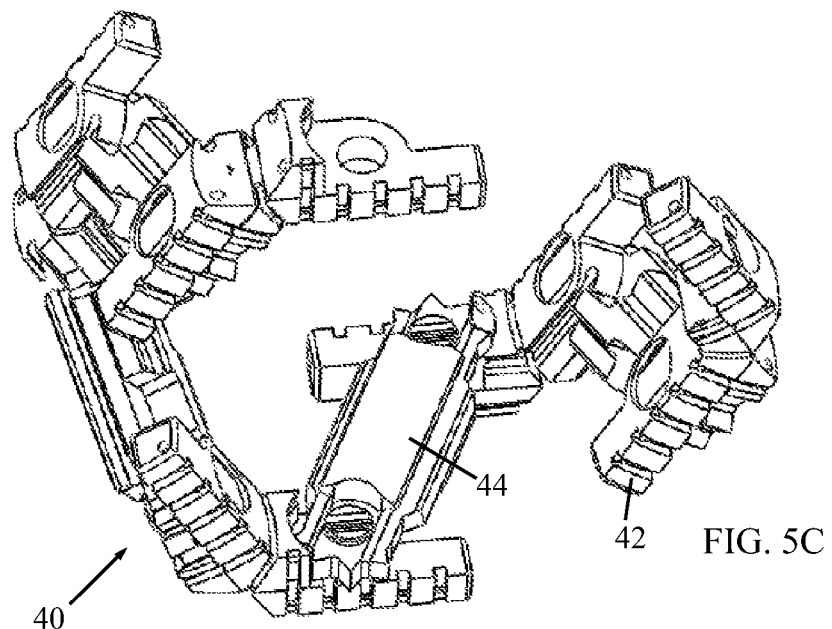
Figure 5D:
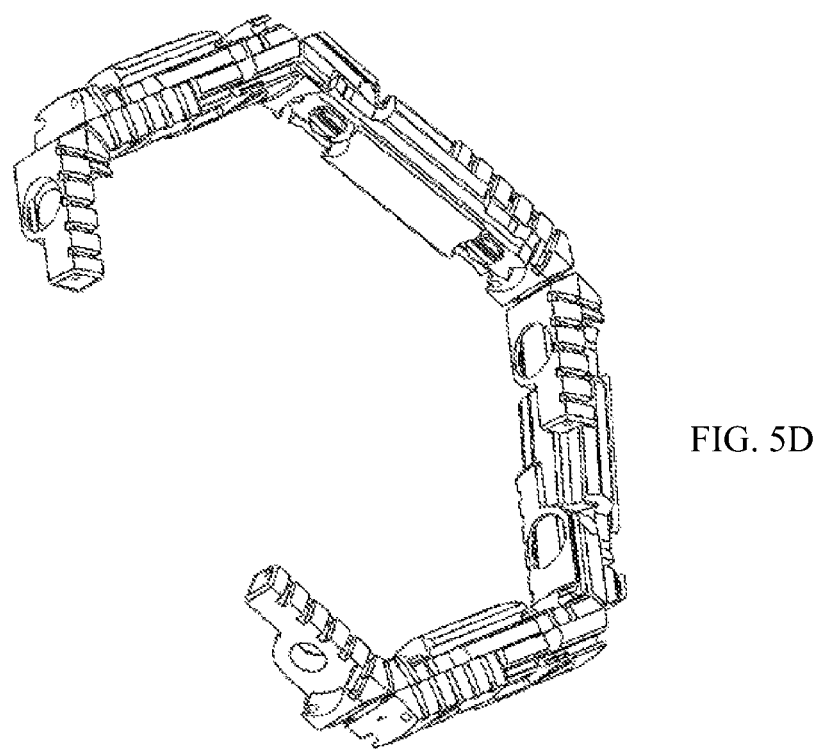
Figure 5E:

The device includes a series of small segments. For example, in FIG. 1A, there are a series of segments 10 interconnected by resilient (elastic, flexible) links 12. The links 12 are thinner than segments 10, and the device is a one-piece (unitary), in-line construction. In FIGS. 1B and 1C, there are a series of resilient (elastic, flexible) segments 14 formed as a spiral or helical spring. Some or all of the segments can be manipulated into a looped shape (or other curved shapes or other arbitrary shapes) and then expanded, either individually or together, to different heights, as seen in FIG. 1D.

The units and links can be made by any tissue compatible material, resorbable or not, or a combination of materials. If hard materials are used, a stronger structure can be obtained for immediate loading after getting the final height. If soft materials are used, they can be shaped as an empty sleeve (or group of variable capacity chambers), which can subsequently be filled to get a final shape which is higher and/or bigger, and also stronger.

The individual segments can have a rough surface, shaped as teeth or spikes, coated with suitable substances, covered by bone friendly materials or metals, for better adherence and/or attachment to the contiguous bone surface. In addition, the use of bonding substances like cement, acrylic, synthetic, biologic or a combination can also be used to ensure the attachment of the device to the intended surface. Additional screws, pins or other fixation means can be added to the device for increased fixation to the vertebral body or to the surface of other bone locations where used.

In one embodiment, shown in FIG. 2A, there are segments 16 made of first and second members 18 and 20 linked to each other by one or more unidirectional or multidirectional hinges 22 or ball-and-socket-like hinges. The first and second members 18 and 20 are shown in FIG. 2A in the contracted position for insertion into the body. The first and second members 18 and 20 may be moved away from each other by pivoting on hinges 22 (the members may be pulled by a pull wire or band, for example) to the expanded, full height position shown in FIG. 2B. Additional segments can be added to cover more volume.

The segments can be expanded all at once, individually or in groups, in one or more dimensions. At the end of the procedure, the final stage of the structure can be locked in place by an internal or external locking mechanism 23 (e.g., pins or teeth that are inserted in the segments to lock them together), by addition of an extra piece for locking, by locking a pulling cable, spring or alike, or by the mechanism included in the delivery system or tool. An intrinsic locking mechanism can be present in the hinging elements of the segment giving a self-locking feature to the device. Alternatively, the final height and transversal expansion may be preserved while still allowing movement of the links.

Other embodiments (FIGS. 3A-3B) may include a hinged, expanding gate having crossed members 24 that pivot at midpoint pivots 26 and endpoint pivots 28. The members 24 are shown in FIG. 3A in the contracted position for insertion into the body; the expanded, full height position is shown in FIG. 3B.

FIG. 4 shows segments 30 linked on alternating sides by flat links 32.

FIGS. 5A-5E illustrate segments 40 pivotally linked to one another by mechanical fasteners 41 (e.g., screws, rivets, pins, etc.). Segments 40 include a roughened (e.g., terraced) surface 42 and a rounded or other shape surface 44, which may be perpendicular, at different angles or parallel to surface 42.

Figure 7A:
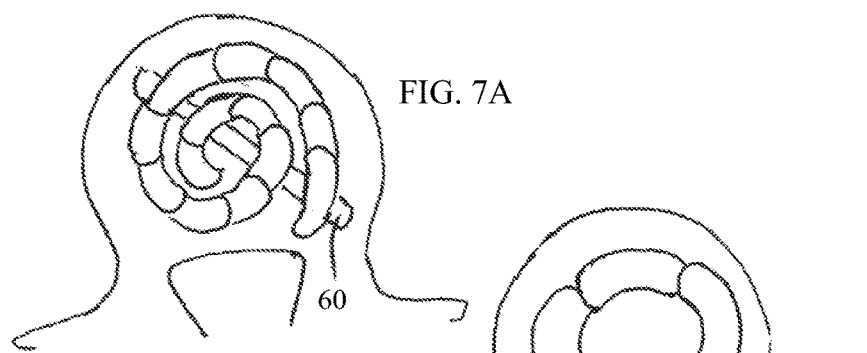
FIGS. 7A-7G are simplified illustrations of bone structural devices of the invention, showing the wide variety of shapes and configurations of the installed, final position of the device.
Figure 7B:
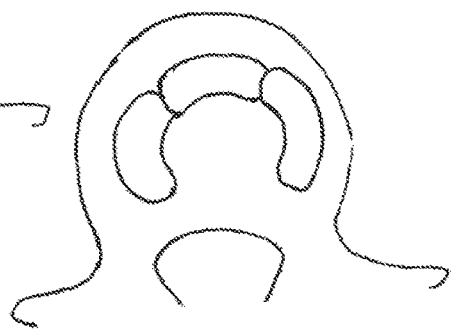
Figure 7C:
Figure 7D:
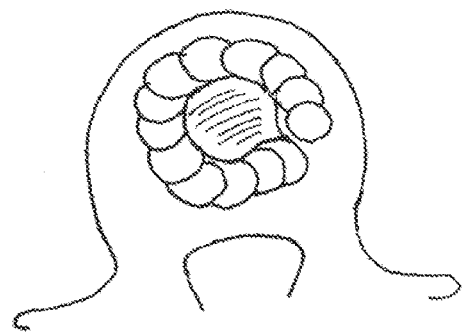
Figure 7E:
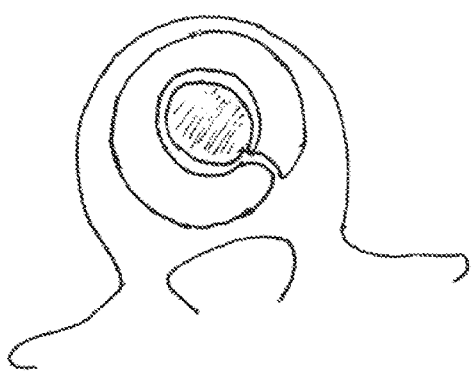
Figure 7F:
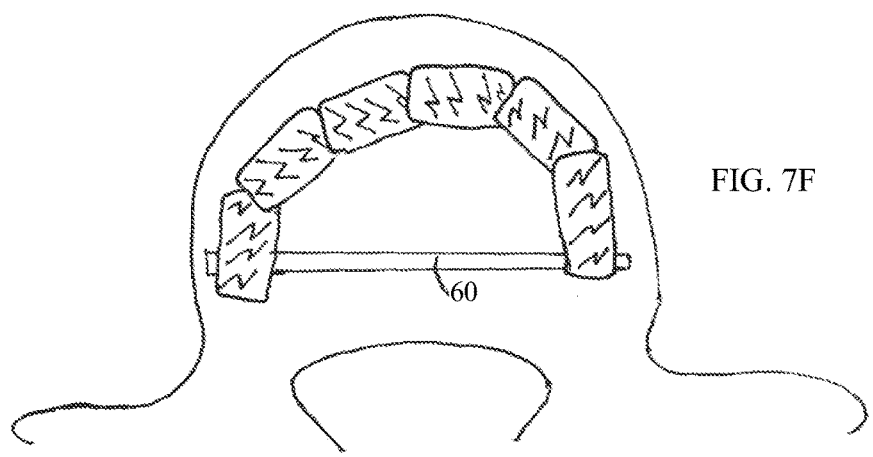
Figure 7G:
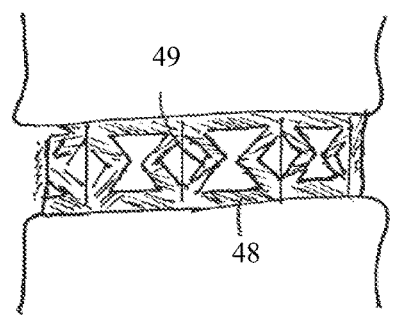

FIG. 7G illustrates segments 48 with resilient, bent side members 49.

FIGS. 8A-8D illustrate segments 50 pivotally linked to one another by elastic (spring-like) members 52.

Thus in accordance with embodiments of the invention, the structure formed with the segments is positioned in the desired location, covering the maximal desired area in the transversal plane and the segments are deployed, expanded, filled, moved or displaced to have a height change (e.g., incremental), one by one, in groups or all at once, controlled by the user, and locked in the desired position, by any means, including mechanical, bonding, suturing, tying, local welding. Sometimes the locking is inherent to the design and there is no need for additional locking. The coverage in the transversal plane may also be done by expandable or deployable mechanisms, in addition to the expansion in height.

Other embodiments will have segments made out of soft material, disposed in a way than can be deployed by filling them with a biocompatible material, natural or synthetic or bone cement. Once the series of segments are in position can be filled one by one or at once changing their height and sometimes shape getting to a final position. In some embodiments, such filling may be done by a hydraulic or pneumatic mechanism of expansion. Then the structure again can be locked to remain in the final position. In an alternative embodiment, the device may be attached to the bone surfaces while allowing a certain range of movement of the device elements. This embodiment can form a closed ring-like structure that can be filled in the center with another soft biocompatible material and may work as a disc replacement by allowing some movement instead of being a fusion device.

The same kind of structures can be made with one unit connected to itself to form a ring-like structure, or sections of several ring pieces connected, which can be filled to gain height to get the desired final configuration. Such a unit can be an expandable sleeve or a folded non-expandable one, which is subsequently filled. In another embodiment, a series of concentric rings or sections of them connected, or a structure of a spiral shape sleeve can be used. In all embodiments, if the central space is filled with bone graft, bone substitutes or other substances, the final result generally leads to bone formation and subsequent fusion of the adjacent vertebrae. The central space can also be filled with a chamber, balloon-like structure that can subsequently be filled with a diversity of agents, leading to a rigid or semi-rigid arrangement to complete the final static structure.

Alternatively, in all embodiments, the central space can be filled with substances other than bone graft or bone substitutes, like natural or synthetic polymers, silicon, free inside the closed device or enclosed in a chamber, soft tissue natural or synthetic scaffolds with or without cells and others leading to a soft, non-rigid tissue, avoiding bone formation and subsequent fusion of the adjacent vertebrae and instead allowing some degree of movement. In addition, materials can be added to avoid blood vessel formation inside the device or others, thus maintaining the soft tissue nature with the intent of avoiding ossification and fusion, for dynamic applications. The central space can also be filled with a chamber, balloon-like structure that can subsequently be filled with a diversity of agents, to complete the final structure.

Figure 6A:
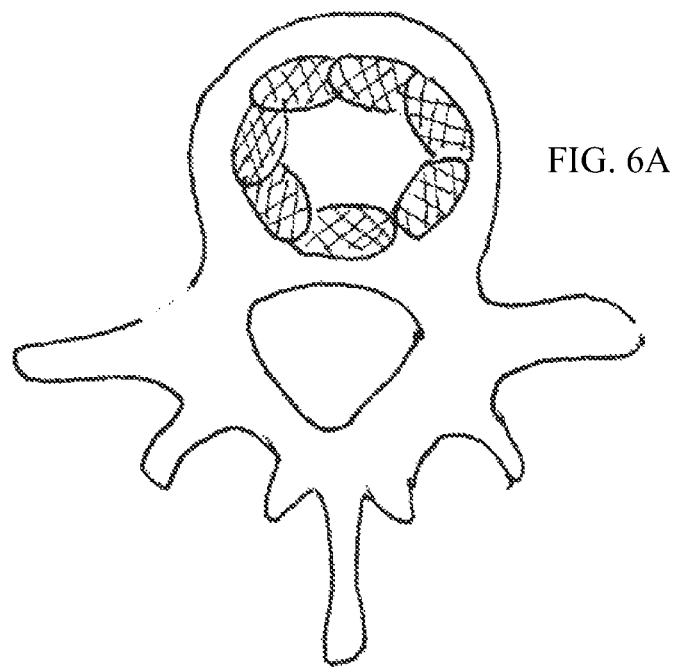
FIGS. 6A and 6B are simplified illustrations of bone structural devices of the invention, respectively installed in an intravertebral space (e.g., in a vertebral body) and an intervertebral space (e.g., disc space).
Figure 6B:
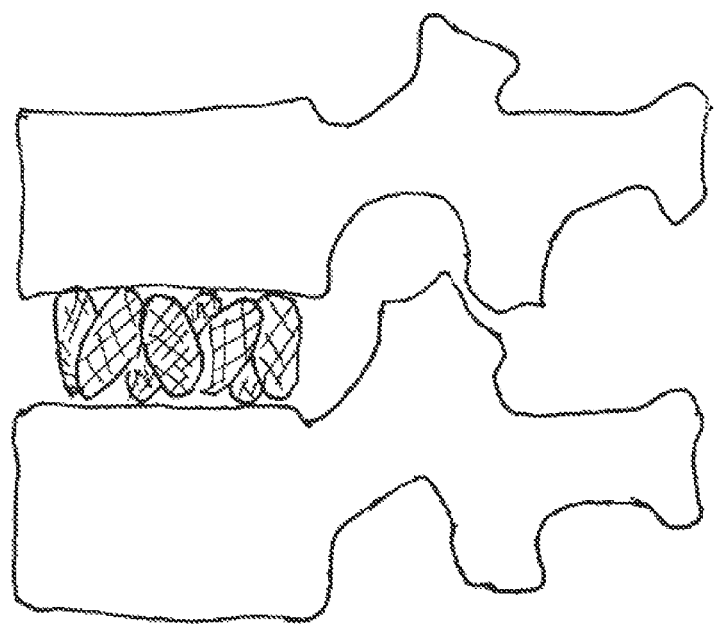

The device may be introduced inside the desired place (e.g., the intervertebral space (FIG. 1D) or the disc space (upper view shown in FIG. 6A and side view in FIG. 6B), or other bones, joints like the knees, ankles or other locations. The segments are linked together with a joint, hinge or other similar element, or may be mounted over a guide wire without a physical link. The segments also can be linked by a plastically and or elastically deformed component without hinges (FIGS. 8A-B and 8C-D). The group of segments of the device can be moved and rearranged to cover as much area as possible, such as but not limited to, a closed loop fashion (FIG. 6A), round, oval, spiral (FIGS. 7A and 7C, both with a closing link 60) or any other shape (FIGS. 7D, 7E and 7F). In some embodiments, a horseshoe shape, with (FIG. 7F) or without (FIG. 7B) closing link 60 can be used.

The device can be guided over a wire, although can be directed to the desired position by an instrument. Any of the alternatives may include a shape memory material (or any other material) guide wire, or as a section of an instrument that may direct the device in a predetermined shape. In addition, the units themselves could be done from a shape memory material. The procedure can be done as a free hand procedure, robotic or computer guided navigation. The display of the device once inserted may create a contained central space with or without communication outside through spaces in between the segments or holes/perforations of the segments themselves. Such spaces can be filled with suitable materials, for static fusion or dynamic results. A full closed ring can be also obtained if needed.

When such structure is made to fit through one pedicle, it can be used to repair a vertebral body fracture known as vertebral compression fracture. Another approach to enter the vertebra may be a hole made in the side or anterior wall of the vertebral body for introduction of the device and further deployment for area coverage and expansion for height control. Also here the filling with bone like material will lead to bone formation and repair of the fracture. In this case also bone cement like PMMA acrylic cement or another compound can be used to fill the void. In other cases, if a vertebral body is surgically removed due to a tumor or any other reason, a proportionate dimension embodiment of the device can be used to fill the space and be used as a vertebral body replacement device in a more minimal invasive way. Again in this case, the resultant structure can be filled with suitable bone like materials for bone formation or bone cement, with or without the aid of additional bone fixation for vertebral fusion of adjacent levels giving a static resultant.

Other bone locations include tibial plateau and tibial plafond fractures, distal radius fractures, calcaneal fractures, distal femur fractures, etc., where the bone is depressed. In addition, in cases of bone necrosis when there is a need of bone elevation of depressed areas, like femoral head, humeral head, distal femur and proximal tibia, also the device can be used with an appropriate filler (such as collagen, bone graft material or biologic cement, for example). In between bones, as in joints, the device can be used as an aid in joint arthrodesis or fusion, maintaining certain position and/or space supplemented with the appropriate filler; also here additional means of fixation as surface coating or treatment and screws or pins can add to the fixation of the device to the adjacent bone surface. When a dynamic situation is required, an embodiment that will allow movement of the device after the transverse expansion and the height expansion is preferred and the filling of the space may include soft materials, to be able to be used as temporary or permanent solutions of joint replacements.

Additional embodiments that allow movement for a disc replacement device may include rigid, solid or soft units connected by suitable links producing a dynamic structure in a mechanic, hydraulic or pneumatic manner with or without the need of filling them, but still with any other way of deployment to gain height, resulting in a device with certain range of movement that resembles the range of the anatomic intervertebral disc.

Figure 9C:
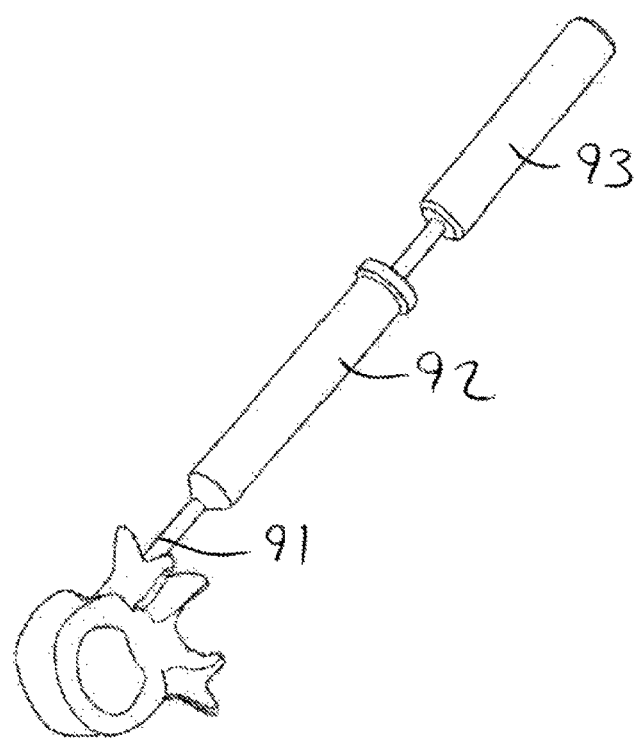
FIGS. 9C and 9D are simplified pictorial and partially cutaway illustrations, respectively, of the insertion device inserting the bone support device of FIGS. 9A-9B into a vertebral structure, in accordance with an embodiment of the present invention.
Figure 9D:
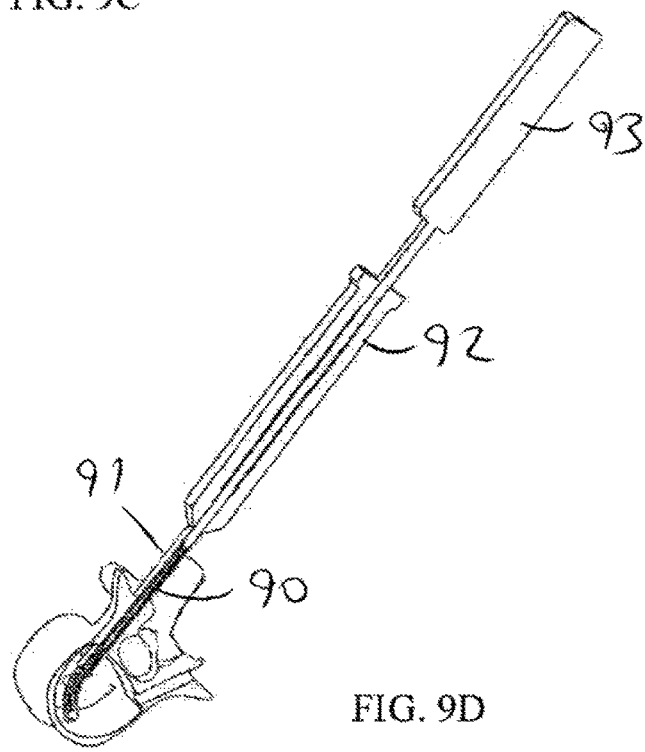

Reference is now made to FIGS. 9A-9D. In this embodiment, a flexible, jointed bone support device 90 (shown schematically, but can be any of the embodiments of the present invention) is placed in a distal outlet port 91 of an insertion device 92. The insertion device 92 includes a plunger 93 for pushing and deploying the bone support device 90 into a vertebral structure, as seen in FIGS. 9C and 9D.

Figure 10A:
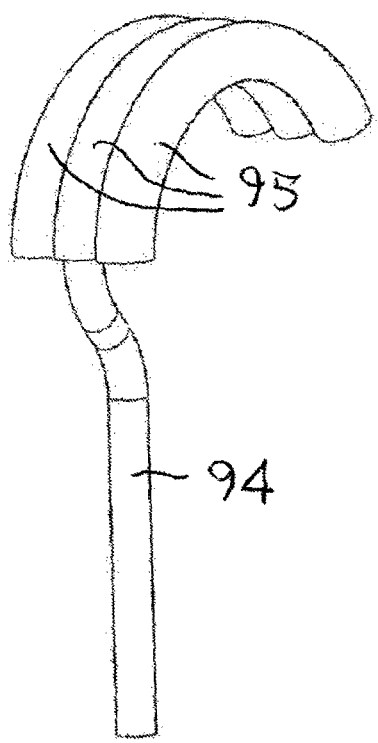
FIG. 10A is a simplified pictorial illustration of an insertion device with a flexible bone support device of the present invention.
Figure 10B:
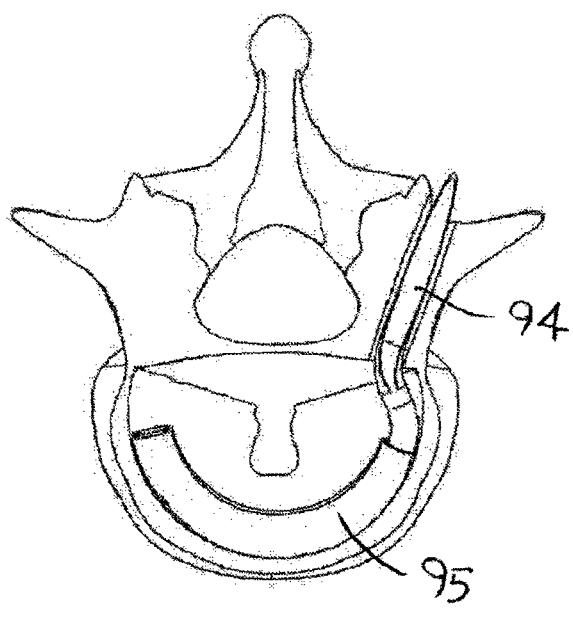
FIGS. 10B and 10C are simplified side-view and perspective illustrations, respectively, of the insertion device inserting the bone support device of FIG. 10A into a vertebral structure, in accordance with an embodiment of the present invention.
Figure 10C:
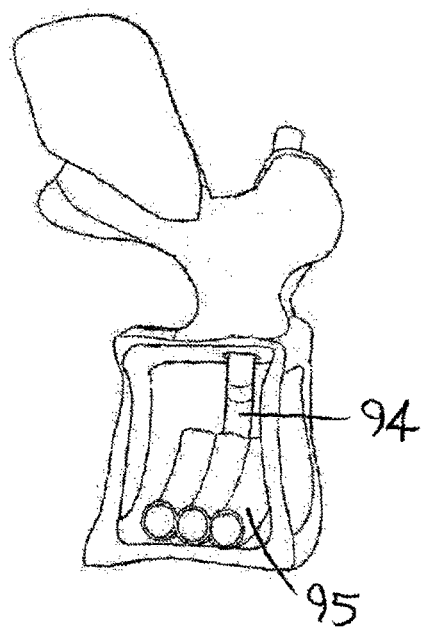

Reference is now made to FIGS. 10A-10C, which illustrate another insertion device 94 with a flexible bone support device 95 of the present invention. Bone support device 95 includes rows of curved segments, laterally adjacent to one another. The insertion device 94 inserts bone support device 95 into a curved channel formed in vertebral structure, as seen in FIGS. 10B-10C.

Figure 11A:
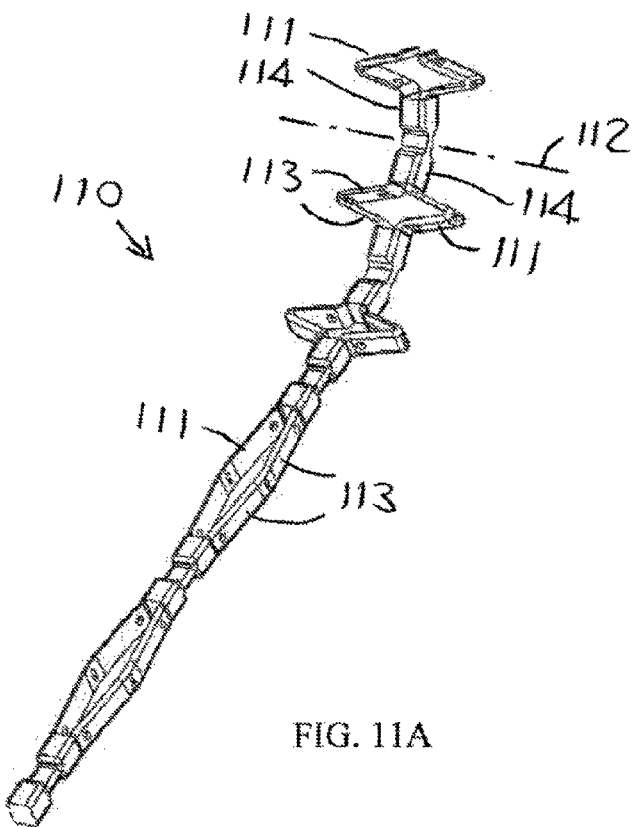
FIG. 11A is a simplified pictorial illustration of a flexible bone support device of the present invention.
Figure 11B:
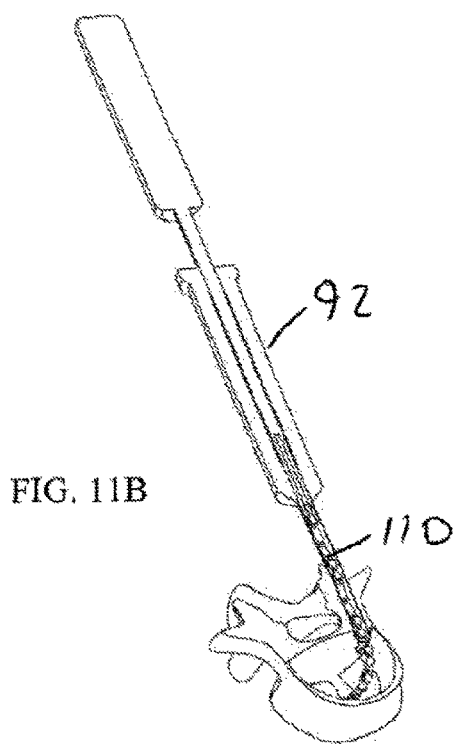
FIGS. 11B and 11C are simplified perspective and side-view illustrations, respectively, of the insertion device inserting the bone support device of FIG. 11A into a vertebral structure, in accordance with an embodiment of the present invention.
Figure 11C:
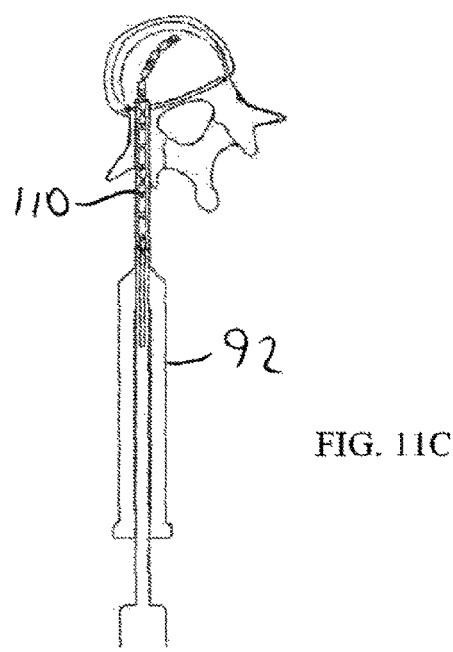

Reference is now made to FIG. 11A, which illustrates a flexible bone support device 110 of the present invention. Bone support device 110 includes a plurality of bone structural segments 111. Adjacent bone structural segments 111 are pivotally connected to one another about a pivot axis 112. The bone structural segments 111 are expandable in height, which is in a direction generally parallel to pivot axis 112. The bone structural segments 111 include struts 113 that are hinged together. The struts 113 extend from links 114, which pivotally connected to one another about pivot axis 112. FIGS. 11B and 11C illustrate the insertion device 92 inserting the bone support device 110 into a vertebral structure, as described above in FIGS. 9C-9D.

Figures 12A, 12B:
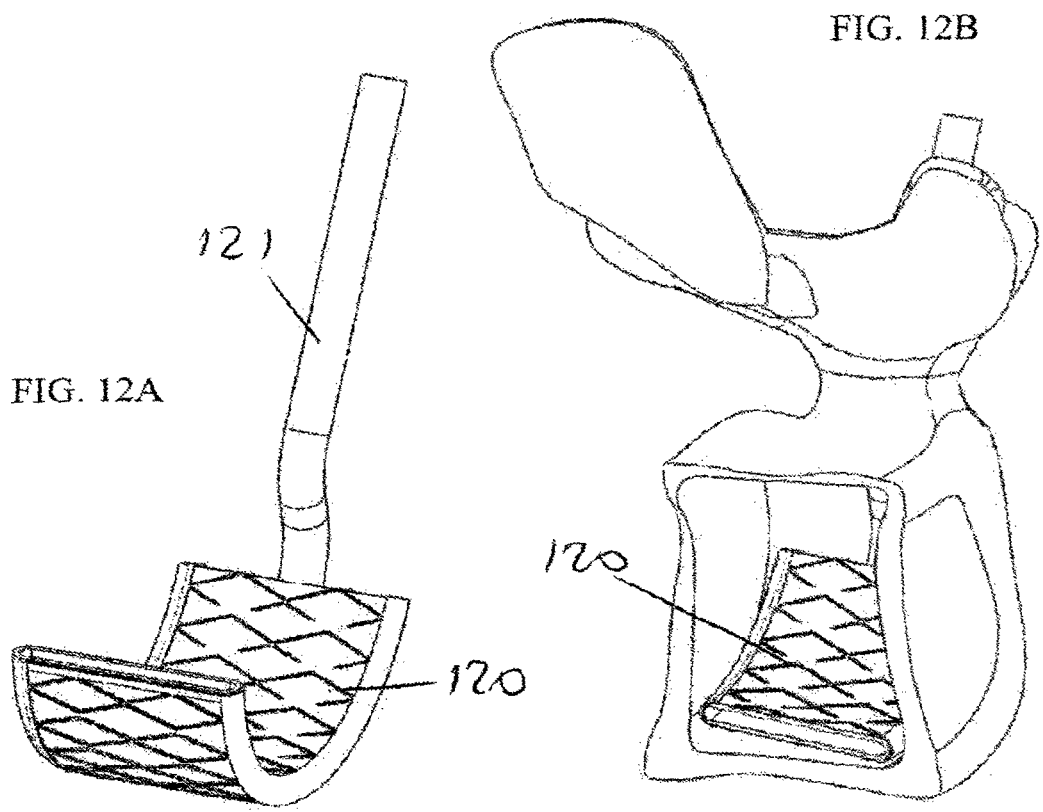
FIG. 12A is a simplified pictorial illustration of a flexible bone support device of the present invention.
FIG. 12B is a simplified perspective illustration of the bone support device of FIG. 12A inserted into a vertebral structure, in accordance with an embodiment of the present invention.

Reference is now made to FIGS. 12A-12B, which illustrates a flexible bone support device 120 of the present invention. Flexible bone support device 120 includes a curved, hollow array of expandable mesh, which can be inserted in the vertebral structure with an insertion device 121.

Figures 13A, 13B:
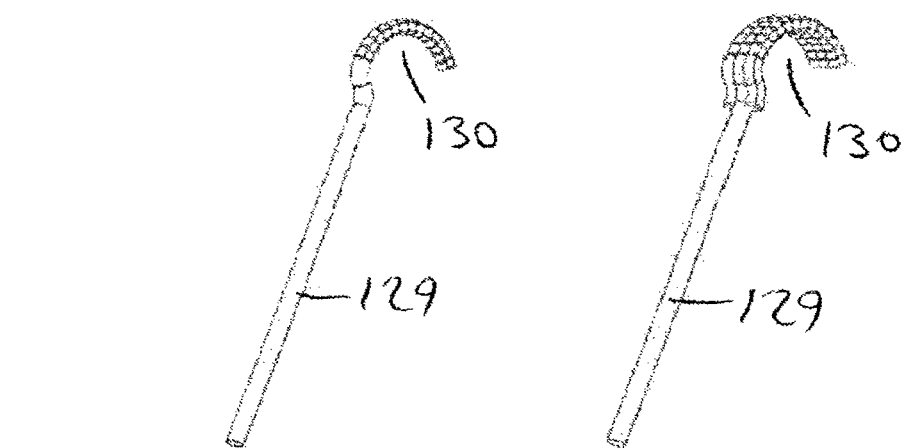
FIGS. 13A and 13B are simplified pictorial illustrations of flexible bone support devices of the present invention, constructed and operative in accordance with two embodiments of the present invention.

Reference is now made to FIGS. 13A-13C, which illustrate another insertion device 129 with a flexible bone support device 130 of the present invention. Bone support device 130 includes one (FIG. 13A) or more (FIG. 13B) rows of curved segments, laterally adjacent to one another. The insertion device 129 inserts bone support device 130 into a curved channel formed in vertebral structure, as seen in FIG. 13C.

Figure 14B:
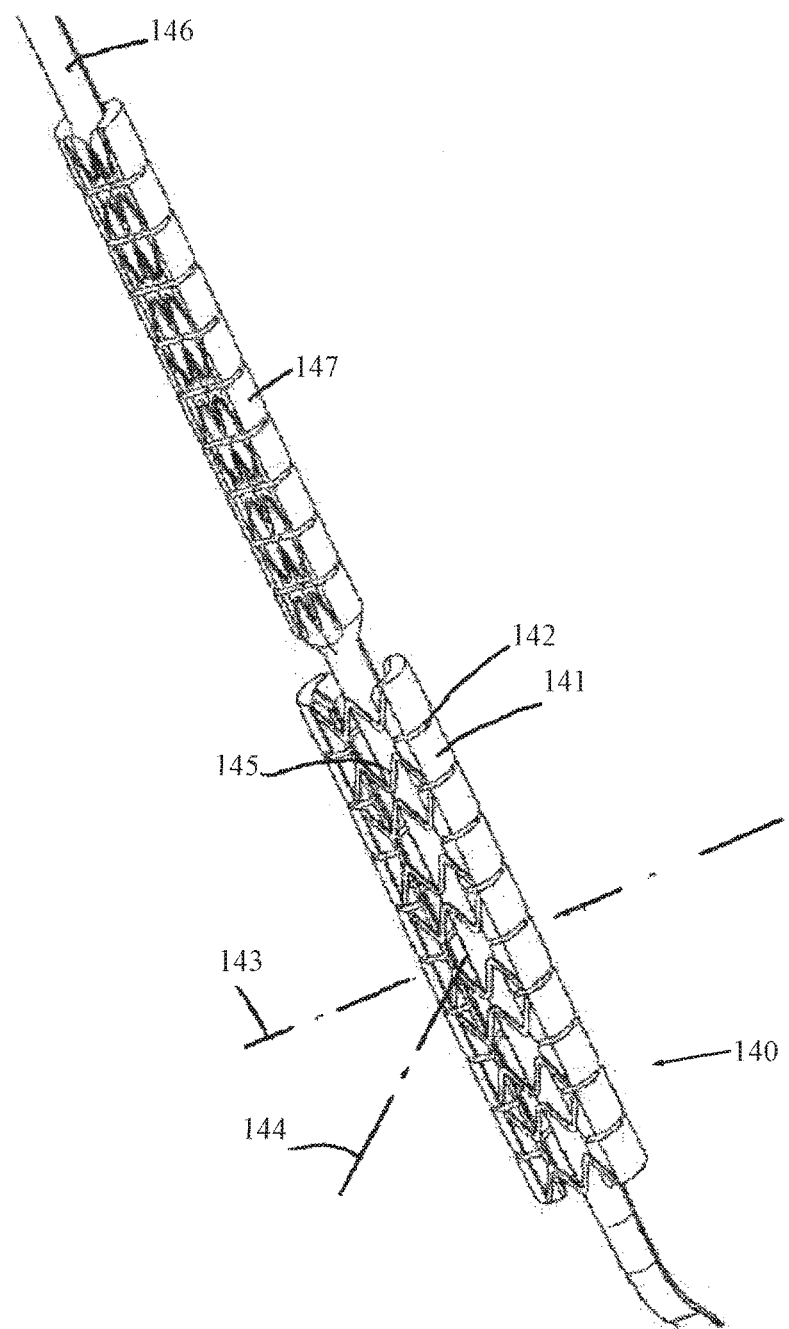
Figure 14C:
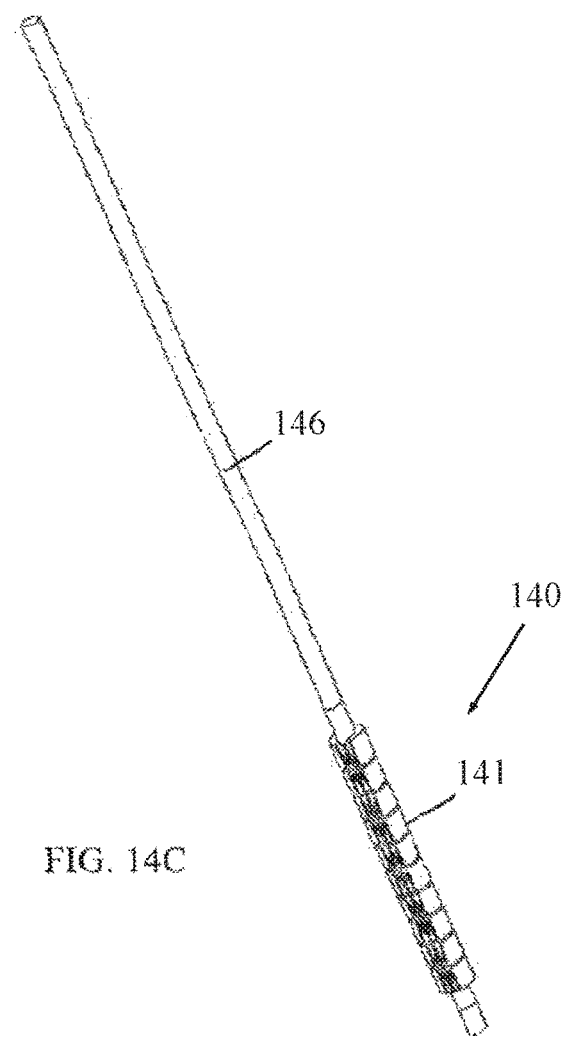
FIG. 14C is a simplified pictorial illustration of the flexible bone support device of FIGS. 14A-14B assembled on an insertion device.

Reference is now made to FIGS. 14A and 14B, which illustrate a flexible bone support device 140, constructed and operative in accordance with an embodiment of the present invention, respectively before and after expansion.

Figure 14D:
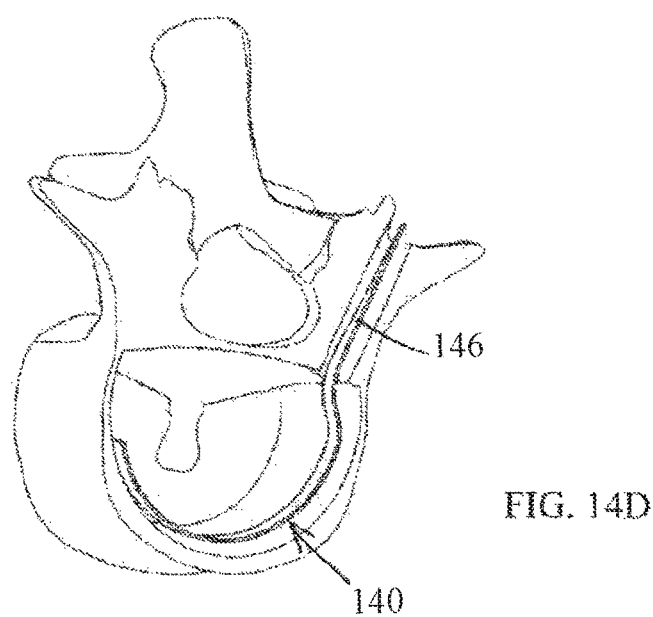
FIG. 14D is a simplified pictorial illustration of inserting the bone support device of FIGS. 14A-14B into a vertebral structure or disc space, in accordance with an embodiment of the present invention.

Bone support device 140 includes a plurality of bone structural segments 141. Adjacent bone structural segments 141 are pivotally connected to one another with hinges 142, which may be unidirectional (hinging about a pivot axis 143) or multidirectional (hinging about pivot axis 143 and another pivot axis 144). The bone structural segments 141 are expandable in height, which is in a direction generally parallel to pivot axis 143 (or alternatively 144). The bone structural segments 141 may include bent link members 145, which are bent in the collapsed position and straightened (at least partially) in the expanded position. The bone structural segments 141 may be assembled on an insertion device 146. A pusher element 147 may be slid or otherwise moved over insertion device 146 to enter the bone structural segments 141 and cause them to expand outwards. The pusher element 147 may be constructed as a plurality of contracted bone structural segments 141. The insertion device 146 may insert bone support device 140 into a vertebral structure, as seen in FIG. 14D.

Figure 14F:
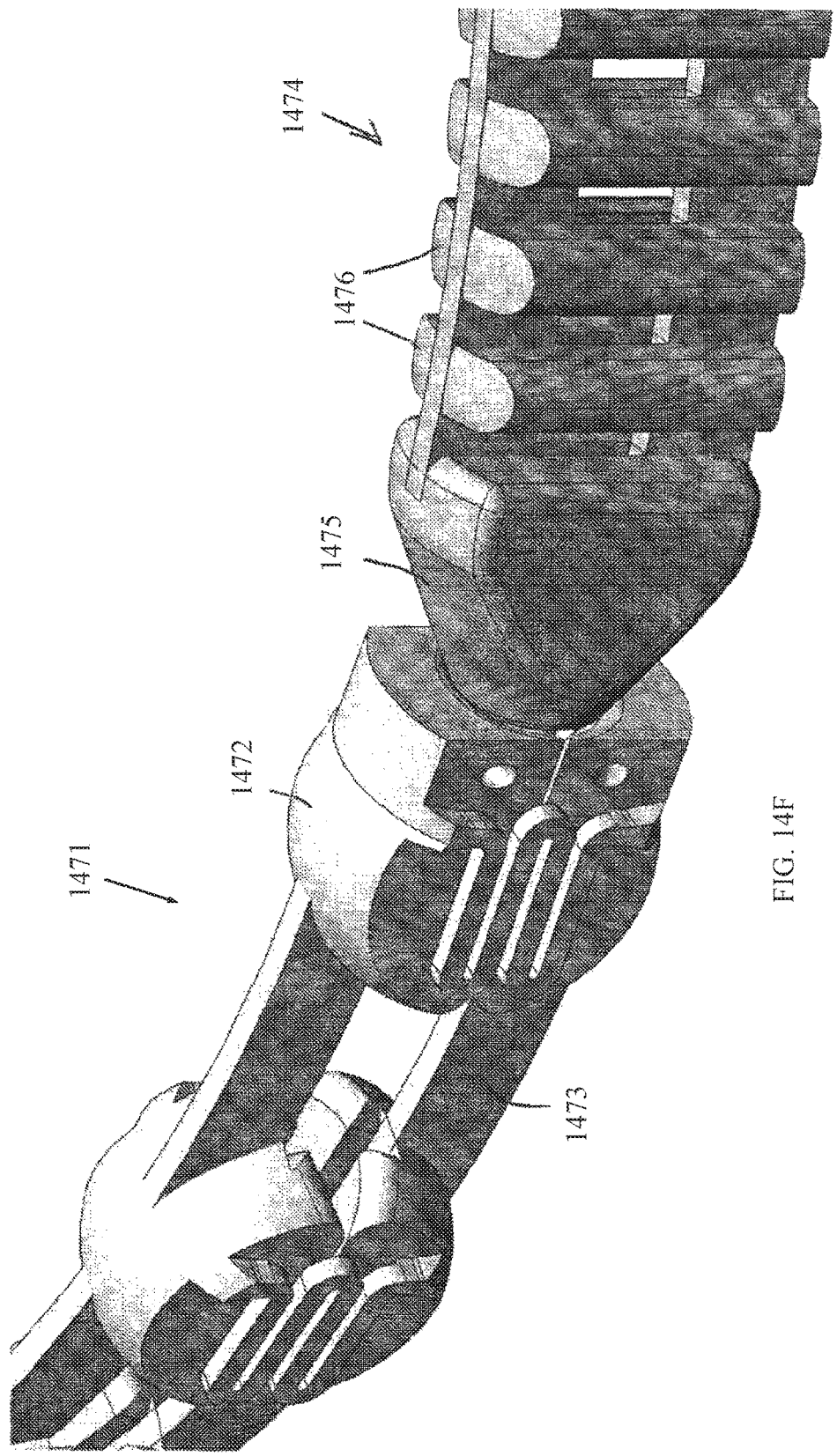

Reference is now made to FIGS. 14E-14F. In this version, there are multiple pusher elements for expanding bone structural segments 141. A first pusher element 1471 includes a series of round lugs 1472 connected by flexible rails 1473. A second pusher element 1474 has a chamfered nose piece 1475 from which extend a plurality of hinged pushers 1476.

Figure 15A:
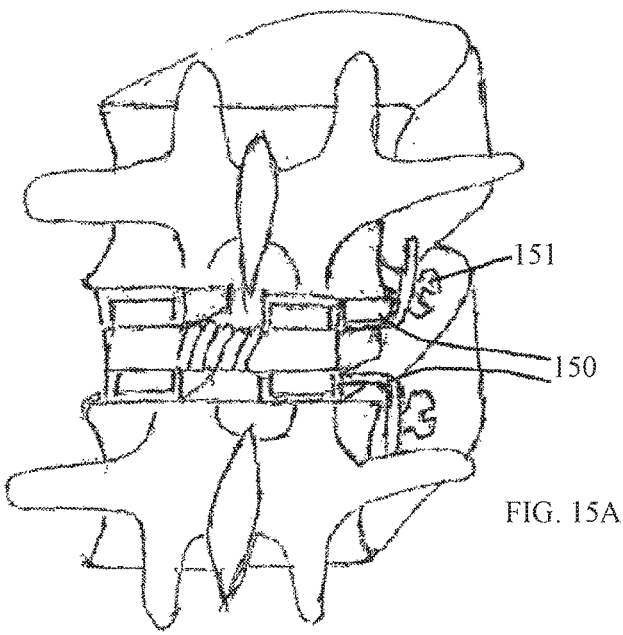
FIG. 15A is a simplified perspective illustration of a bone structural support device, constructed and operative in accordance with an embodiment of the present invention.
Figure 15B:
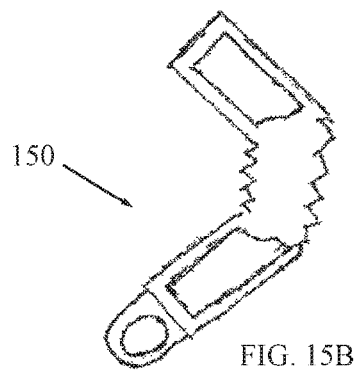
FIGS. 15B and 15C are simplified top-view and perspective illustrations, respectively, of segments of the bone structural support device of FIG. 15A.
Figure 15C:
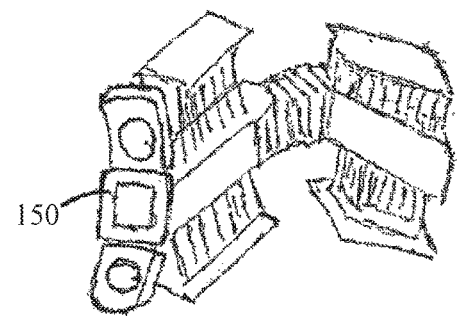

Reference is now made to FIGS. 15A-15C. Any of the bone structural support devices of the invention may be provided with one or more fastening flanges 150. Flange 150 has mounting provisions for inserting therethrough fastening hardware 151 (FIG. 15A), such as but not limited to, screws or any other suitable fasteners or adhesive. Flange 150 may be straight or bent.

Figure 16A:
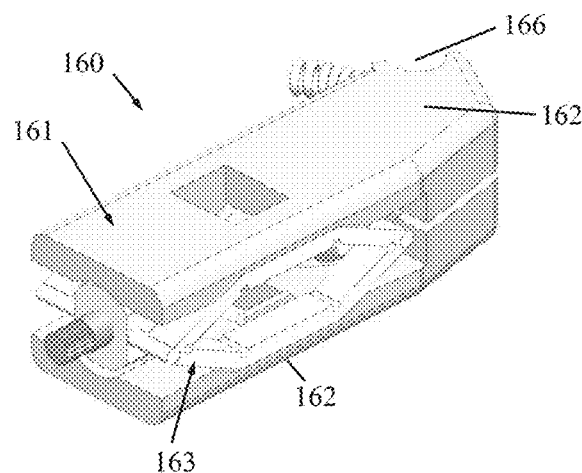
FIGS. 16A and 16B are simplified illustrations of a flexible bone support device, constructed and operative in accordance with another embodiment of the present invention, respectively before and after expansion.
Figure 16B:
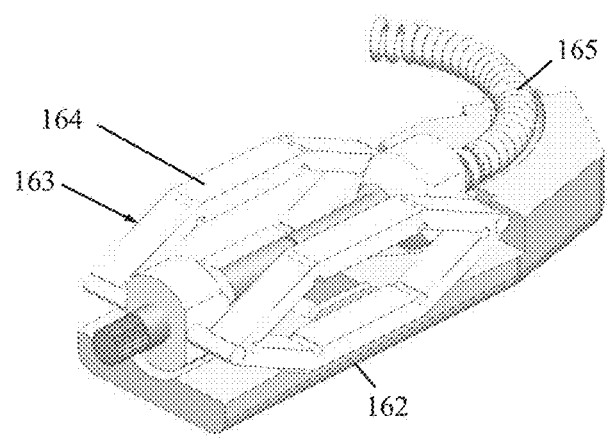

Reference is now made to FIGS. 16A and 16B, which illustrate a flexible bone support device 160, constructed and operative in accordance with an embodiment of the present invention, respectively before and after expansion.

Bone support device 160 includes a plurality of bone structural segments 161, each of which includes a pair of parallel support plates 162, which may be expanded by an intermediate jacking mechanism 163. The jacking mechanism 163 may include one or more hinged cages 164 which can be raised and lowered by a flexible screw drive 165. Adjacent bone structural segments 161 are pivotally connected to one another with hinges 166.

Figure 17B:
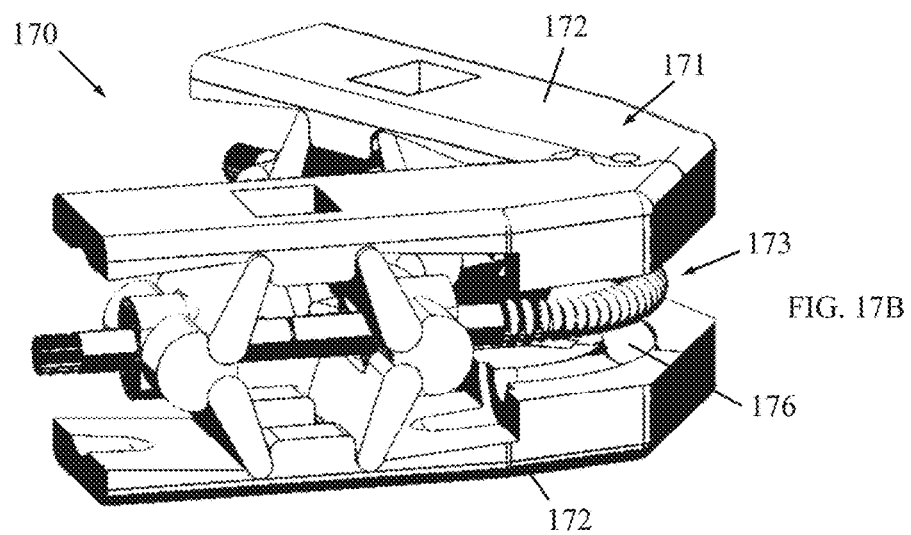
FIGS. 17A and 17B are simplified illustrations of a flexible bone support device, constructed and operative in accordance with another embodiment of the present invention, respectively before and after expansion.
Figure 17A:
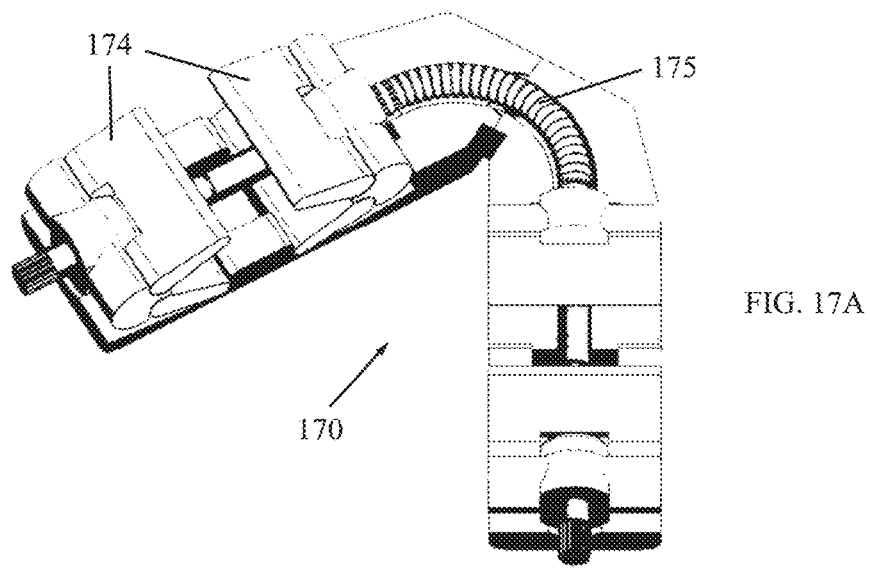

Reference is now made to FIGS. 17A and 17B, which illustrate a flexible bone support device 170, constructed and operative in accordance with an embodiment of the present invention, respectively before and after expansion.

Similar to bone support device 160, bone support device 170 includes a plurality of bone structural segments 171, each of which includes a pair of parallel support plates 172, which may be expanded by an intermediate jacking mechanism 173. The jacking mechanism 173 may include hinged flaps 174 which can be raised and lowered by a flexible screw drive 175. Adjacent bone structural segments 171 are pivotally connected to one another with hinges 176.

Figure 18A:
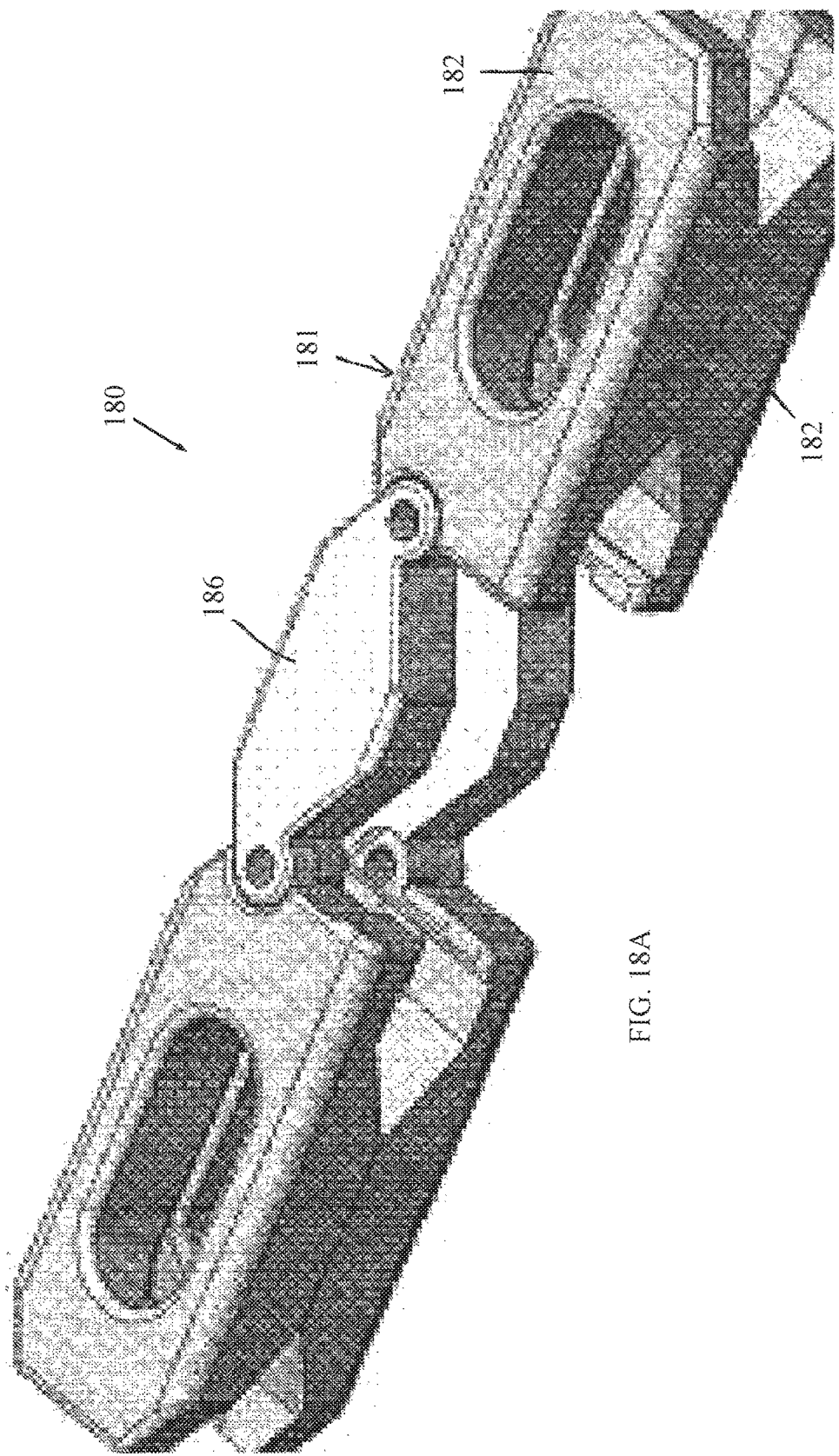
FIGS. 18A and 18B are simplified illustrations of a flexible bone support device, constructed and operative in accordance with another embodiment of the present invention, respectively before and after expansion.
Figure 18B:
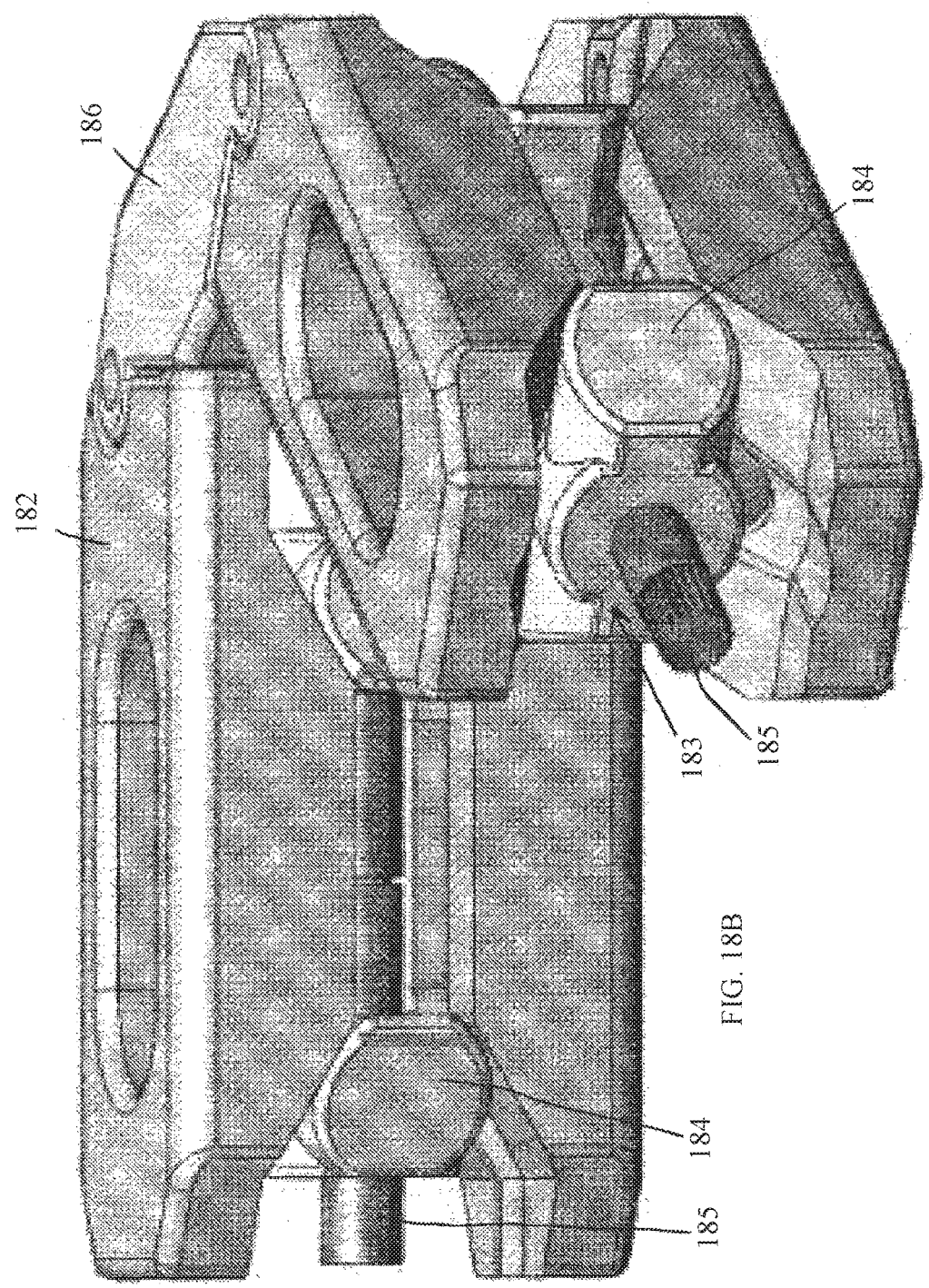

Reference is now made to FIGS. 18A and 18B, which illustrate a flexible bone support device 180, constructed and operative in accordance with an embodiment of the present invention, respectively before and after expansion.

Bone support device 180 includes a plurality of bone structural segments 181, each of which includes a pair of parallel support plates 182, which may be expanded by a jacking mechanism 183 (omitted for simplicity in FIG. 18A). The jacking mechanism 183 may include wedges 184 which can be moved in and out by a hydraulic or pneumatic expander (or could be a screw drive) 185. Adjacent bone structural segments 181 are pivotally connected to links 186.

Figure 19A:
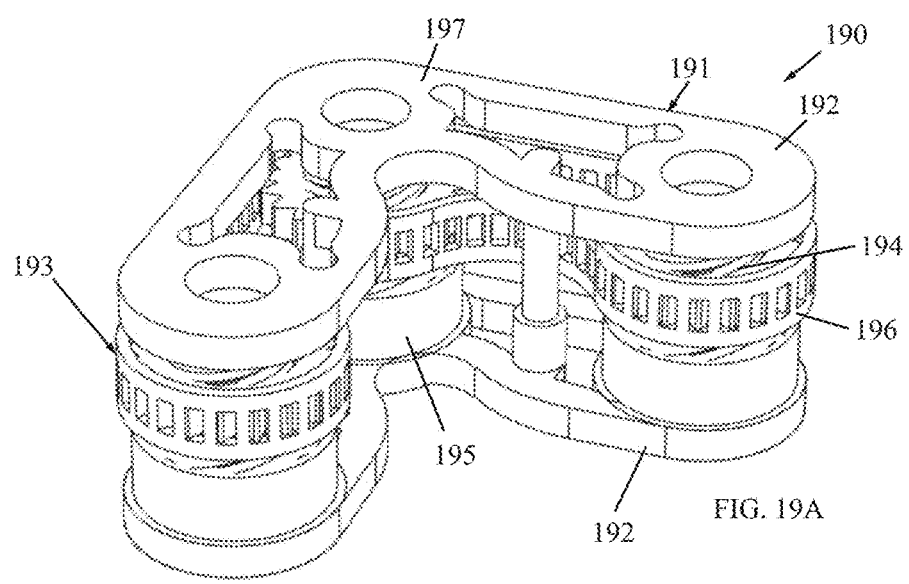
FIGS. 19A and 19B are simplified illustrations of a flexible bone support device, constructed and operative in accordance with another embodiment of the present invention, respectively before and after expansion.
Figure 19B:
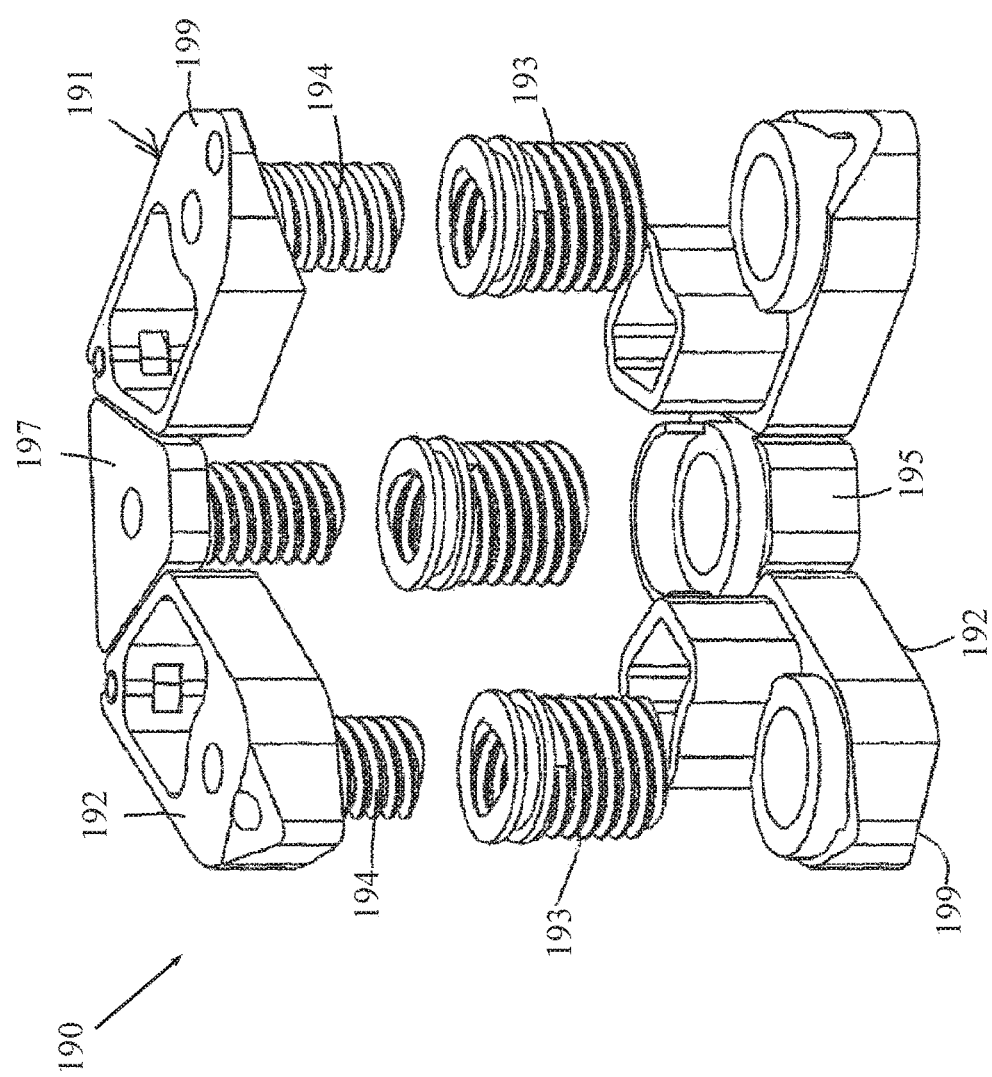

Reference is now made to FIGS. 19A and 19B, which illustrate a flexible bone support device 190, constructed and operative in accordance with an embodiment of the present invention, respectively before and after expansion.

Bone support device 190 includes a plurality of bone structural segments 191, each of which includes a pair of parallel support plates 192, which may be expanded by a gearing, toothed or screw mechanism 193. The mechanism 193 may include one or more gears or screws that mesh with and turn lifting screws 194. The gears and lifting screws may be turned by a belt 196 or by another element, such as pull wires, for example. Adjacent bone structural segments 191 are pivotally connected to one another with hinges. One or both of the hinges may be a pivoting hinge 195. Additionally or alternatively, one or both of the hinges may be a flexible hinge 197 that deforms when the bone structural segments 191 flex or bend with respect to one another. As seen in FIG. 19B, one or both of parallel support plates 192 may have an extension 199 which is not parallel to parallel plate 192. This may help in matching bone contours.

The scope of the present invention includes both combinations and subcombinations of the features described hereinabove as well as modifications and variations thereof which would occur to a person of skill in the art upon reading the foregoing description and which are not in the prior art.

What is claimed is:

1. A bone structural device comprising:
a plurality of bone structural segments, each of said bone structural segments comprising a pair of parallel support plates, wherein adjacent bone structural segments are pivotally connected to one another about a pivot axis, and wherein said bone structural segments are expandable in height, which is in a direction generally parallel to said pivot axis, and wherein said bone structural segments are expandable by an intermediate jacking mechanism that comprises at least one set of hinged flaps which are raised and lowered by a flexible screw drive connected to said hinged flaps.

2. The bone structural device according to claim 1, wherein each of said hinged flaps comprises an upper flap pivotally connected to a lower flap at a pivot, said upper flap comprising an upper abutting end opposite to said pivot that abuts against an upper one of said support plates and said lower flap comprising a lower abutting end opposite to said pivot that abuts against a lower one of said support plates.

3. The bone structural device according to claim 2, wherein said at least one set of hinged flaps comprises two sets of said hinged flaps, and the upper and lower abutting ends of one set of said hinged flaps faces the upper and lower abutting ends of the other set of said hinged flaps.

4. The bone structural device according to claim 2, wherein said flexible screw drive passes through said pivots.

5. The bone structural device according to claim 1, wherein said bone structural segments are linked to each other by one or more hinges.

* * * * *

UNITED STATES PATENT AND TRADEMARK OFFICE
CERTIFICATE OF CORRECTION

PATENT NO. : 10,307,254 B2
APPLICATION NO. : 14/130950
DATED : June 4, 2019
INVENTOR(S) : Levy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1123 days.

Signed and Sealed this
Second Day of June, 2020

Andrei Iancu
*Director of the United States Patent and Trademark Office*